(12) United States Patent
Bortolin et al.

(10) Patent No.: US 8,062,846 B2
(45) Date of Patent: Nov. 22, 2011

(54) APPARATUS FOR ISOLATING A NUCLEIC ACID FROM A SAMPLE

(75) Inventors: Laura T. Bortolin, Devens, MA (US); Lalitha Parameswaran, Burlington, MA (US); James Harper, Boston, MA (US); Johanna Bobrow, Somerville, MA (US); Mark A. Hollis, Concord, MA (US); Drew Chapman Brown, Towson, MD (US); Eric Scott Clasen, Hillsborough, NJ (US); John Calvin Schmidt, Baltimore, MD (US)

(73) Assignees: Massachusetts Institute of Technology, Cambridge, MA (US); Smiths Detection-Edgewood, Inc., Edgewood, MD (US)

( * ) Notice: Subject to any disclaimer, the term of this patent is extended or adjusted under 35 U.S.C. 154(b) by 0 days.

(21) Appl. No.: 11/804,598

(22) Filed: May 18, 2007

(65) Prior Publication Data

US 2008/0131949 A1 Jun. 5, 2008

Related U.S. Application Data

(63) Continuation of application No. 10/616,904, filed on Jul. 10, 2003, now abandoned.

(60) Provisional application No. 60/395,109, filed on Jul. 10, 2002.

(51) Int. Cl.
*C12Q 1/68* (2006.01)
*B01D 35/00* (2006.01)
*B01L 99/00* (2010.01)

(52) U.S. Cl. ......... 435/6.1; 422/534; 422/535; 422/537; 422/558

(58) Field of Classification Search .................... None
See application file for complete search history.

(56) References Cited

U.S. PATENT DOCUMENTS

| | | |
|---|---|---|
| 5,234,809 A | 8/1993 | Boom et al. |
| 5,496,562 A | 3/1996 | Burgoyne |
| 5,660,984 A | 8/1997 | Davis et al. |
| 5,707,850 A | 1/1998 | Cole |
| 5,756,126 A | 5/1998 | Burgoyne |
| 5,804,684 A | 9/1998 | Su |
| 5,807,527 A | 9/1998 | Burgoyne |
| 5,840,169 A | 11/1998 | Anderson |
| 5,863,801 A | 1/1999 | Southgate et al. |
| 5,910,246 A | 6/1999 | Walter et al. |
| 5,939,259 A | 8/1999 | Harvey et al. |
| 5,972,386 A | 10/1999 | Burgoyne |
| 5,976,572 A | 11/1999 | Burgoyne |
| 5,985,327 A | 11/1999 | Burgoyne |
| 6,037,465 A | 3/2000 | Hillebrand et al. |
| 6,103,192 A | 8/2000 | Stapleton et al. |
| 6,110,428 A * | 8/2000 | Borst et al. .................... 422/101 |
| 6,168,922 B1 | 1/2001 | Harvey et al. |
| 6,218,176 B1 | 4/2001 | Berthold et al. |
| 6,232,464 B1 | 5/2001 | Lange |
| 6,264,814 B1 | 7/2001 | Lange |
| 6,374,684 B1 | 4/2002 | Dority |
| 6,428,962 B1 | 8/2002 | Naegele |
| 6,431,476 B1 | 8/2002 | Taylor et al. |
| 6,440,725 B1 | 8/2002 | Pourahmadi et al. |
| 6,673,631 B1 | 1/2004 | Tereba et al. |
| 6,699,434 B1 * | 3/2004 | Lukasik et al. ................. 422/33 |
| 2002/0042125 A1 | 4/2002 | Peterson et al. |
| 2003/0129614 A1 | 7/2003 | Parameswaran et al. |

FOREIGN PATENT DOCUMENTS

| | | |
|---|---|---|
| EP | 0 757 106 A2 | 2/1997 |
| JP | 09-019292 | 1/1997 |
| JP | 2000-300262 | 10/2000 |
| WO | WO 99/13976 | 3/1999 |
| WO | WO 0105510 A1 * | 1/2001 |
| WO | WO 01/45522 A1 | 6/2001 |
| WO | WO 0208727 A1 * | 1/2002 |
| WO | WO 0218902 A1 * | 3/2002 |
| WO | WO 02/38758 A1 | 5/2002 |
| WO | WO 03/033740 A2 | 4/2003 |

OTHER PUBLICATIONS

Hultman et al. Direct solid phase sequencing of genomic and plasmid DNA using magnetic beads as solid support. Nucleic Acids Research (1989) 17(13): 4937-4946.*

Andreotti, P., "Portable Swab Sample Processor (SSP) and Analyzer for Rapid Detection of Biothreat Agents," *Defense Advanced Research Projects Agency, Tissue Based Biosensors, Advanced Diagnostics, Activity Detection Technologies Principle Investigator Conference 2002*, DARPA, Miami, Florida, Feb. 18-21, 2002.

"Cepheid Granted U.S. Patent Covering GeneXpert(R) Cartridge," at http://biz.yahoo.com, Jun. 5, 2002.

(Continued)

*Primary Examiner* — Young J Kim
*Assistant Examiner* — Angela M Bertagna
(74) *Attorney, Agent, or Firm* — Hamilton, Brook, Smith & Reynolds, P.C.

(57) ABSTRACT

An apparatus for preparing a nucleic acid component of a sample for amplification includes a porous support having an agent that deactivates a nucleic acid amplification inhibitor component of the sample. The apparatus further includes a housing with an opening and defining an interior. The interior of the housing is in fluid communication with the porous support, and at least a portion of a fluid directed through the opening is directed through at least a portion of the porous support. The apparatus also includes a magnetic substrate for separating nucleic acid from a sample.

9 Claims, 16 Drawing Sheets

OTHER PUBLICATIONS

Cepheid News; "Cepheid Collaborates on Major U.S. Postal Contract for Bio-threat Detection—Pilot Program to Employ GeneXpert® DNA-Detection System," at http://www.cepheid.com/pages/press/020513.html, Sunnyvale, CA, May 13, 2002.

Cepheid Technology; "Fluidic Systems" at http://www.cepheid.com, Jun. 5, 2002.

How GeneXpert Automates Sample Preparation, at http://media.corporate-ir.net, Jun. 5, 2002.

Levy, S., "A Fully Automated High-Throughput Nucleic Acid Purification System Using Silica Coated Magnetic Bead Technology," *Laboratory Robotics Interest Group, New England Chapter, Poster Session*, Mar. 26, 2002, from http://www.lab-robotics.org/New_England/Posters/LRIG-New%20England%20Posters%20March%2026,2002.pdf.

Parameswaran, L., "Development of Recovery Techniques for Organisms and Nucleic Acids from Complex Samples", *Third Annual Biodetection Technologies 2003 International Symposium*, from http://www.knowledgepress.com/event/12111105.htm.

Schmidt, J.C., "A Portable Biodetection System Incorporating Semi-Automated Sample Preparation," *Detection Technologies—The Next Generation in Identification and Analysis*, Arlington, Virginia, Dec. 5-6, 2002, http://www.knowledgepress.com/events/7191716.htm.

Taylor, Michael T., et al., "Lysing Baterial Spores by Sonication through a Flexible Interface in a Microfluidic System," *Anal. Chem.*, 73:492-496(2001).

Tu, Shu-I, et al., "Applications of Time-Resolved Fluoroimmunoassay to Detect Magnetic Bead Captured *Escherichia coli* 0157:H7," *Journal of Rapid Methods and Automation in Microbiology*, 9:71-84 (2001).

Xtrana: Products: Nucleic Acid Testing; "SCIP: Self Contained Integrated Particle," http://www.xtrana.com, Jun. 5, 2002.

Brush, Michael D., "Numerous Kits Prepare Samples for PCR Amplification the Quick and Not-so-Dirty Way," *The Scientist* 14(13):1-5 (2000).

Smail, et al. "Rapid, Cost-effective Gene Mutation Screening for Carnitine Palmitoyltransferase II Deficiency Using Whole Blood on Filter Paper," *Clinical Chemistry*, 1999 45(11):2035-2038.

Fiscus, et al. "Quantitation of Human Immunodeficiency Virus Type 1 RNA in Plasma by Using Blood Dried on Filter Paper," *Journal of Clinical Microbiology*, Jan. 1998, 36(1):258-260.

Chandler, et al., "Automated nucleic acid isolation and purification from soil extracts using renewable affinithy microcolumns in a sequential injection system," *Talanta* 1999, 49:969-983.

Itoh, et al., "Automated Filtration-Based High-Throughput Plasmid Preparation System," *Genome Research*, 1999, 9:463-470.

Deggerdal, et al. Rapid Isolation of PCR-ready DNA from blood, bone marrow and cultured cells, based on paramagnetic beads, *Biotechniques* 22(3): 554-557, published 1997.

Supplementary European Search Report from PCT/US2003/21480, date of mailing Nov. 17, 2010.

* cited by examiner

US 8,062,846 B2

APPARATUS FOR ISOLATING A NUCLEIC ACID FROM A SAMPLE

RELATED APPLICATION

This application is a Continuation of U.S. Utility application Ser. No. 10/616,904, filed Jul. 10, 2003, now abandoned, which claims the benefit of U.S. Provisional Application No. 60/395,109, filed Jul. 10, 2002. The entire teachings of the above applications are incorporated herein by reference.

GOVERNMENT SUPPORT

The invention was supported, in whole or in part, by Lincoln Contract Number F19628-95-C-0002 from Defense Directorate of Research and Engineering. The Government has certain rights in the invention.

BACKGROUND OF THE INVENTION

Nucleic acids generally are analyzed by polymerase-chain-reaction (PCR) procedures. The presence of PCR inhibitors, such as often encountered in samples collected for medical diagnosis, during forensic investigations or in defense-related applications, hinders PCR-amplification.

It is difficult, for example, to extract amplifiable DNA from soil or slurry raw samples, in particular, from samples that include clays or other soils that have high organic content.

Conventional techniques for extracting amplifiable nucleic acids from samples generally are complicated, labor-intensive, and require laboratory facilities and equipment. Many existing protocols also require toxic reagents, such as phenol and chloroform.

One material developed for DNA isolation, in particular in conjunction with handling blood samples, is a chemically treated cotton matrix available from Schleicher and Schuell, Inc., of Keene, N.H., under the tradename of IsoCode®. IsoCode® based protocols adapted to handle raw samples, such as described above, still require laboratory equipment, external reagents and entail numerous steps (including two oven drying cycles). Moreover, as with other approaches, the samples are susceptible to sample contamination.

Therefore, a need exists for a method for preparing a nucleic acid component of a sample for amplification that is faster, less complicated and less labor-intensive than existing protocols. A need also exists for an apparatus for conducting such a method. In particular, there exists a need for a portable, self-contained device, suitable for field use, that can be employed for preparing a nucleic acid component of a sample for amplification and can be used for analyzing, storing or archiving the resulting nucleic acid component.

SUMMARY OF THE INVENTION

The invention generally is related to a method and apparatus for preparing a nucleic acid component of a sample for amplification.

The method includes the steps of separating the sample from raw sample components through means that includes a magnetic substrate, contacting the sample with a porous support that deactivates a nucleic acid amplification inhibitor component of the sample and directing a fluid through the porous support, whereby the nucleic acid component of the sample is directed through at least a portion of the porous support and is separated from the porous support, thereby preparing the nucleic acid component for amplification.

The apparatus for preparing a nucleic acid component of a sample for amplification includes a porous support including an agent that deactivates a nucleic acid amplification inhibitor component of a sample contacting the porous support; a housing having an opening and defining an interior, said interior being in fluid communication with the porous support, whereby at least a portion of a fluid directed through the opening is directed through at least a portion of the porous support and separates at least a portion of a nucleic acid component of a sample contacting the porous support from the support, thereby preparing the nucleic acid component for amplification; and separating means for separating the sample from raw sample components and for depositing the nucleic acid component at the porous support which said means includes a magnetic substrate.

In preferred embodiments, the porous support includes an agent such as a chaotropic salt. Surface treatment of the magnetic substrate can result in preferential attachment of a sample that includes a nucleic acid component to be prepared for amplification thereby separating the sample from raw components, such as, for example, soil particles.

The invention has numerous advantages. For example, the invention can be used with raw samples, as collected in the field, and can process solids, semi-solids, slurries, swipes, liquids or aerosols. By employing the invention, a nucleic acid component in a raw sample can be prepared for amplification in a reduced number of steps that can be completed in minutes. Forced flow-through of the elution fluid is faster than diffusive movement through a porous substrate that deactivates a nucleic acid amplification inhibitor and obviates or minimizes the need for heat. Addition of external reagents also is reduced or entirely eliminated, lessening the potential for sample contamination. Furthermore, the method of the invention can be conducted using water (or water and buffer compounds) as the only reagent. By employing the apparatus of the invention, samples can be collected and prepared in the field, with minimum transport considerations and the collection and preparation steps can be conducted using heavy gloves and protective gear. The samples prepared can be archived and/or can be amplified using standard equipment, as known in the arts. The apparatus of the invention is light-weight, compact, can be subjected to decontamination of its outer surfaces and can be manufactured economically. Parts of the apparatus are disposable. Furthermore, the apparatus provides versatility to sample collection and allows the removal of raw sample components as well as handling of samples that can be collected and processed without separating the sample from raw sample components through means that include a magnetic substrate.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention. All parts and percentages are by weight unless otherwise indicated.

DETAILED DESCRIPTION OF THE INVENTION

Figure 1A:
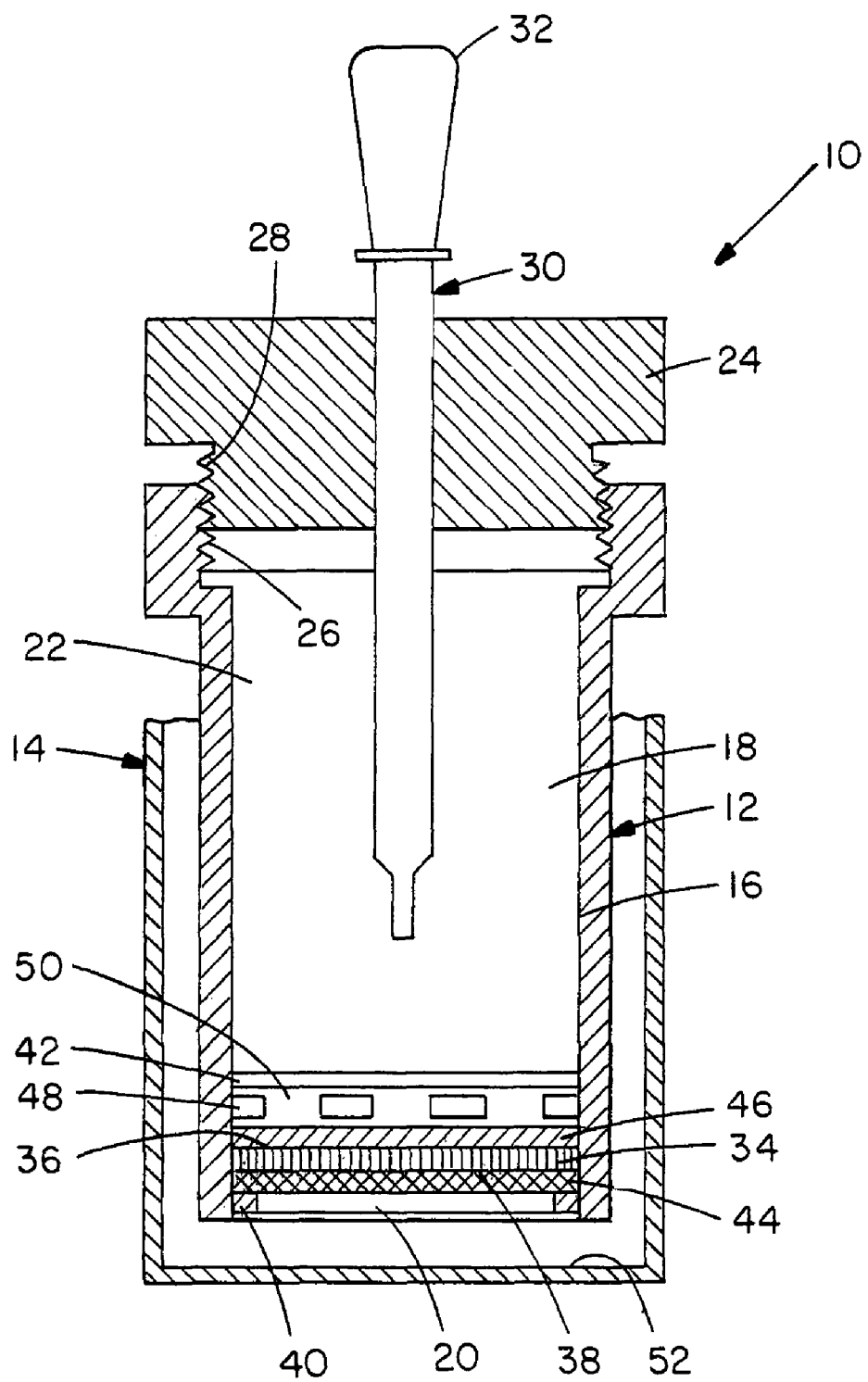
FIG. 1A is a longitudinal cross sectional view of an embodiment of an assembly that can be employed in one embodiment of the apparatus of the invention and to conduct the method of the invention.

A description of preferred embodiments of the invention follows.

The invention generally is related to a method and apparatus for preparing a nucleic acid component in a sample for amplification.

The method includes the steps of contacting a sample that includes a nucleic acid component with a porous support that deactivates a nucleic acid amplification inhibitor component of the sample and directing a fluid through the porous support, whereby the nucleic acid component of the sample is directed through at least a portion of the porous support and is separated from the porous support, thereby preparing the nucleic acid component for amplification. The sample is separated from raw sample components through means that include a magnetic substrate, e.g., magnetic beads.

The sample includes a nucleic acid component and a nucleic acid amplification inhibitor component. As used herein, the term nucleic acid includes poly or oligo nucleotides. Examples of nucleic acids include, but are not limited to, DNA, RNA, fragments thereof, isotopically tagged nucleic acids or any combinations thereof.

The nucleic acid amplification inhibitor can be a PCR inhibitor or a compound or material that is capable of damaging nucleic acids. Examples include, but are not limited to, hemoglobin, humic acid, fulvic acid, divalent cations, chelating molecules, enzymes, proteins and others. One or more nucleic acid amplification inhibitors can be present in the sample.

The sample is contacted with a porous support. For example, liquid samples are brought to wet the porous support by dispensing the sample onto the porous support or by immersing the porous support in the sample.

Solid samples can be contacted with the porous support by wiping the solid support over the solid sample, or over a solid surface containing the sample thereby smearing or accumulating sample present on a solid surface onto the porous support. Optionally the porous support can be first wetted with a liquid, e.g., water, and then used to wipe over the solid sample or over a solid surface containing the sample. Slurries can be brought into contact with the porous support by immersion or wiping.

Gas samples, e.g., air, that contain bacteria, spores, viruses or other nucleic acid components, as well as aerosols, also can be contacted with the porous support. For instance, a gas sample can be brought into contact with the porous support by means such as a blower, or by using vacuum suction to draw the gas sample towards and onto the porous support. The porous support can be wetted prior to being brought into contact with a gas sample.

Generally, nucleic acids that contact the porous support are not irreversibly bound to it. For example, nucleic acids can be stabilized by contact with the porous support and released from the porous support during elution.

Nucleic acid amplification inhibitors, e.g., a polymerase chain reaction (PCR), inhibitors, that contact the porous support are deactivated. In one embodiment of the invention, the porous support also retains solid contaminants. Preferably, the porous support also is capable of lysing or killing cells, spores, bacteria and other microorganisms, of inactivating RNases or DNases, or of lysing cells or spores to release nucleic acid. The porous support also can bind one or more chemical compound, e.g., salts, used in preparing the nucleic acid component for amplification.

Generally, the porous support is water permeable. The porous support can be rigid or flexible and can be in the form of a pad, mat, disk, plug, thin layer, or can be in another suitable form. The porous support can be fabricated from silk, paper, cotton cloth, or other woven or non-woven materials, such as, for instance, natural or synthetic polymers, e.g., polyesters, polypropylene and others.

Generally, the porous support includes one or more agents that deactivate(s) a nucleic acid amplification inhibitor, e.g., a PCR inhibitor. The agent can change the secondary, tertiary or quaternary structure of biomolecule. The agent can induce precipitation, irreversible binding to the porous support or can denature nucleic acid amplification inhibitors. Deactivated components of the inhibitor are retained by the porous support or are soluble fragments that do not interfere with nucleic acid amplification procedures.

The agent also can disrupt cell membranes and cellular proteins to allow access to nucleic acid material present on or in the target cells.

To form the porous support, the agent can be impregnated into a suitable substrate or it can be otherwise incorporated or held by it. Substrates that are coated or chemically treated with the agent also can be employed. Methods for impregnating, chemically treating or coating substrates are known in the art.

In a preferred embodiment, the agent is a chaotropic salt. Examples of chaotropic salts include, but are not limited to, guanidine salts, e.g., guanidine isothiocyanate, guanidine thiocyanate, guanidine hydrochloride, sodium iodide, sodium perchlorate, potassium iodide, sodium (iso)thiocyanate, urea, or any combinations thereof.

Suitable porous supports are described in U.S. Pat. No. 5,496,562, issued to Burgoyne, on Mar. 5, 1996; U.S. Pat. No. 5,756,126, issued to Burgoyne on May 26, 1998; U.S. Pat. No. 5,807,527, issued to Burgoyne on Sep. 15, 1998; U.S. Pat. No. 5,972,386, issued to Burgoyne on Oct. 26, 1999; U.S. Pat. No. 5,976,572, issued to Burgoyne on Nov. 2, 1999; U.S. Pat. No. 5,985,327, issued to Burgoyne on Nov. 16, 1999; U.S. Pat. No. 5,939,259, issued to Harvey, et al., on Aug. 17, 1999; and U.S. Pat. No. 6,168,922, issued to Harvey, et al., on Jan. 2, 2001. The entire teachings of the above-referenced patents are incorporated herein by reference.

One specific example of a suitable porous support is paper available under the trade name of IsoCode® chemically treated matrix, which can be obtained from Schleicher and Schuell, Inc., Keene, N.H.

The method of the invention includes the step of directing a fluid through the porous support. Preferably, the fluid is water and can include buffer compounds. Examples of buffer compounds include, but are not limited to TE (tris-EDTA), TAE (tris-acetic acid EDTA), TBE (tris-boric acid-EDTA), and deionized water. (Where EDTA is ethylene diamine tetraacetic acid.) Other fluids, such as, alcohols, also can be employed.

Directing generally is by active means that result in flow-through conditions of the fluid through at least a portion of the porous support. The fluid can be directed through the porous support, or portion thereof, by applying a force upon the fluid, for example by pressing a piston, lid, plunger, flexible membrane or other mechanical means upon the fluid. In a closed chamber, fluid can be directed through the porous support by compressing gas, e.g., air, above the fluid, for example by pressing a plunger or a flexible membrane. A pressure gradient also can be employed, e.g., by using a pump, vacuum or compression means to draw fluid through the porous support. The resulting flow-through of the fluid, together with a nucleic acid component, through the porous support, can be in any direction with respect to the porous support. In a preferred embodiment, fluid is directed from the face to which the sample is applied, through the porous support, to the opposite face.

Upon directing the fluid through the porous support, or through a portion thereof, the nucleic acid component in the sample is directed through at least a portion of the porous support. Nucleic acid amplification inhibitors and other contaminants described above are inactivated by and/or retained onto the porous support, while the nucleic acid component is separated from the support, generally with the eluted fluid. The nucleic acid component of the sample is thus prepared for amplification.

Optionally, compounds that are not present in the raw sample, but are introduced or generated during the preparation of the nucleic acid component for amplification, also can be removed. An example of such a compound includes a salt. For instance, salts can be removed by treating the fraction eluted from the porous support by a membrane designed for salt removal. Such desalting membranes are known in the art. Suitable examples include, but are not limited to, Sephadex™ cross-linked dextran gel beads, Sepharose™ cross-linked dextran gel beads, or ion-exchange membranes.

Proteins also can be removed. For example, proteins can be removed by using sepharose beads, cellulose beads or membranes.

Additional steps optionally can be conducted to enhance the separation of the nucleic acid component from the porous support, in particular with samples that contain low (trace) levels of nucleic acid(s).

One method for enhancing recovery of the nucleic acid component from the porous support is by applying heat. Heating can be in an oven, by immersion in an external hot bath, by heating coils, by blowing a hot gas or by other suitable means. The sample can be heated to a temperature in a range of between about 60° Centigrade (C) and about 95° C. In many cases, heating is at about 95° C. for about 30 minutes.

In another embodiment of the invention, recovery of the nucleic acid component from the porous support is enhanced by applying an electric field (electroelution) across the porous support containing the nucleic acid component of the sample. DNA, for example, has a net negative charge when in solution. In the presence of liquid with conductive ions and an electric field produced by two oppositely charged electrodes, wherein the negative electrode is applied to the porous support containing the nucleic acid component of the sample, DNA, for example, can be eluted from the porous support and caused to migrate to the positive electrode.

Preferably, the electrodes are coated to prevent irreversible adhesion of nucleic acids onto the electrodes. The electric field preferably is applied while the sample is in contact with the porous support. The electric field can be supplied by a direct current (DC) power supply. Generally, the voltage differential employed is in a range from about 0.5 volts (V) to about 20 V, generally for less than about 10 minutes, preferably for about 5 minutes. Current flow generally is less than about 1 nano ampere (nA). After the nucleic acids have been collected from the porous support, the voltage polarity may be reversed for a short period of time, preferably less than 5 seconds, to detach nucleic acids collected onto the positive electrode and resuspend them into the eluate.

A sample that is processed as described above is separated from raw sample components through means that include a magnetic substrate. Raw samples often are collected on location, for example, during forensic investigations, defense-related applications or in the medical field. Such samples can include plant or animal tissue, blood, bodily fluids, feces, saliva, urine, buccal swabs, bacteria, microorganisms, pathogens, spores, fungi, viruses, food, cells, soils, e.g., clays, combinations thereof, and other organic and inorganic materials.

The method of the invention is particularly well suited to handle raw samples that preferably are liquids, solids, semi-solids, slurries or wipes. A raw sample that is a slurry or liquid can be brought into contact with the magnetic substrate without further dilution. A raw sample in solid form or a swipe sample preferably is combined with water, buffer, or another suitable solvent. The resulting solution or suspension is then brought into contact with the magnetic substrate. Raw components in samples that are aerosols also can be removed, for example by directing the raw sample onto the magnetic substrate by a blower or by other means known in the art.

Raw components include, for example, sand, soil, dust, clay particles, debris, food particles, cells, proteins and other inorganic or organic materials. Preferably, removal of raw sample components results in a sample that has an increased concentration of nucleic acid component in comparison to the raw sample.

Examples of magnetic substrates that can be employed include magnetic beads, shavings, pellets or other suitable bodies that can be extracted from the raw sample through the application of a magnetic field, such as produced, for example, by a permanent magnet. Materials that can be employed to form the magnetic substrate include rare earth-based magnetic materials. In one example the magnetic substrate includes iron oxide, also known as magnetite.

In one embodiment, the magnetic substrate is the form of magnetic beads that can have a sphere diameter in the range of from about 100 nanometers to about 1 millimeter. In a preferred embodiment, magnetic beads have a diameter in the range of from about 250 nanometers (nm) to about 10 microns ($\mu$m). The size of the magnetic substrate can be selected according to particular applications. For instance, some bacterial spores have a size in the order of about 1 $\mu$m; preferred beads for capturing such spores have a diameter larger than 1 $\mu$m.

In one embodiment, it is the raw components that are captured onto the magnetic substrate and are thereby separated from the sample that includes the nucleic acid component and that is to be further processed. Preferably, the sample that includes the nucleic acid component is attached or captured onto the magnetic substrate, while the raw components are not.

The preferential capture of some of the components present in the raw sample can be accomplished by surface treatment, impregnation or coating of the magnetic substrate.

For example, magnetic beads that have hydrophobic surfaces can be employed to capture spores. Examples of such magnetic beads include polystyrene latex beads such as those available commercially from Polysciences, Warrington, Pa. or from Spherotech, Libertyville, Ill.

Silica ($SiO_2$)-treated or silica-based magnetic substrates, such as, for example, superparamagnetic silica beads, which are available, for instance, from Polysciences, Warrington, Pa., can be employed to capture nucleic acids, e.g., DNA.

Magnetic substrates that have hydrophilic surfaces can be employed to capture vegetative bacterial cells, nucleic acids, and other components. Example of such magnetic substrates include beads available commercially under the trade names of Biomag™ carboxyl from Polysciences, Warrington, Pa. or beads having designation MC02N/2928 from Bangs Laboratory, Inc., Fishers, Ind.

In one example, the magnetic substrate is coated with streptavidin. Streptavidin-coated magnetic beads are commercially available, for example from Stratech Scientific Ltd., Soham, England, e.g. those having Catalog #BNN1101.

In other embodiments, specific materials present in the raw sample can be physically adsorbed onto the magnetic substrate. In yet other embodiments, specific coatings can be employed to chemically bind one or more materials present in the raw sample.

Combinations of magnetic beads, having different surface properties, also can be used. For instance, a raw sample can be contacted with silica coated magnetic beads, to capture DNA and with hydrophobic magnetic beads to capture spores.

Stirring, shaking or other means for agitation can be used, for example, to enhance contact and adherence to the magnetic substrate. Manual shaking or suitable equipment can be employed, as known in the art.

The magnetic substrate is extracted from the raw sample by placing the magnetic substrate in a magnetic field, thereby separating raw sample components from the sample. The magnetic field can be generated by a permanent magnet, such as, for instance, a rare earth magnet.

In one embodiment of the invention, the magnetic field is used in combination with gravity. For example, the sample to be further processed, attached to magnetic beads, is forced upwards towards a magnet positioned above the raw sample/magnetic beads mixture, while gravity favors sedimentation of at least a portion of the raw components, e.g., sand or soil particles.

Removal of the magnetic field releases magnetic beads. In one embodiment, magnetic beads that have attached sample on their surface are brought into contact or deposited onto with the porous support. Liquid, e.g., water or buffer solution can be added to the beads to enhance transfer of the sample from the beads to the porous support. In another embodiment, the sample is washed from the magnetic substrate and then brought into contact with the porous support. Other techniques for removing the sample from the magnetic beads, such as, for instance, desorption, changes in buffer pH or in salt concentration of the buffer also can be employed.

The invention also is related to an apparatus suitable for preparing a nucleic acid component of a raw sample for amplification.

The apparatus includes a porous support that deactivates a nucleic acid amplification inhibitor component of a sample contacting the porous support and a housing. The housing has an opening and defines an interior that is in fluid communication with the porous support, whereby at least a portion of a fluid directed through the opening is directed through at least a portion of the porous support and separates at least a portion of a nucleic acid component of a sample contacting the porous support from the support, thereby preparing the nucleic acid component for amplification.

For example, the porous support includes an agent that deactivates the nucleic acid inhibitor component of the sample, such as, for instance a chaotropic salt. Preferably the agent also kills cell or spores, deactivates DNases or RNases or lyses cells or spores to release nucleic acid.

One embodiment of the apparatus of the invention includes assembly 10, shown in FIG. 1A. Assembly 10 includes housing 12 and container 14.

Assembly 10 is constructed in any suitable size. In a preferred embodiment of the invention, assembly 10 is sufficiently small to be portable, such as hand-held, and is suited for field applications. For instance, the largest dimension of assembly 10 can range from about 3 to about 13 centimeters. In one embodiment, assembly 10 is suitable for handling 50 microliter samples. Larger assembly 10 also can be constructed. In another embodiment, assembly 10 is constructed to be compatible with a commercially available PCR machine.

Assembly 10 is fabricated from any suitable material, preferably, a material that does not react with the substances with which it comes in contact. In a preferred embodiment, assembly 10 is fabricated, in whole or in part, from a plastic material, such as, for example, polycarbonate, nylon, polydialkylsiloxanes, polyethylene or polypropylene terephthalates, polytetrafluoroethylene and others. Assembly 10 also can be fabricated, in whole or in part, from glass or a metal such as, steel, aluminum and other materials. Combinations of materials also are suitable for fabricating assembly 10. Assembly 10 can be disposable after a single use.

Housing 12, includes tube 16 which defines interior region 18. Tube 16 can be cylindrical but can have another suitable shape. Tube 16 has ends 20 and 22. End 20 is open. End 22 is provided with means for receiving cap 24. Means for receiving cap 24 are, for instance, threaded groves 26 that match threaded grooves 28 on cap 24.

Other means for sealing end 22 also can be employed. For example, in an embodiment not shown in FIG. 1A, end 22 is sealed by a press-fitted cap. Septum closures, such as known in the pharmaceutical arts also can be employed. In still another embodiment, also not shown in FIG. 1A, the housing is constructed in an integrated fashion, with one sealed end. For instance, the tube can terminate in a narrow, elongated sealed ending that can be detached or broken, as known in the medical and pharmaceutical arts.

In a preferred embodiment, cap 24 is provided with dropper 30. In FIG. 1A, dropper 30 is a medicine dropper and includes bulb 32 that can be squeezed and released to collect liquid from interior region 18 of tube 16. Other dropper designs also can be employed as known in the art. Access to interior region 18 of tube 16 also can be provided by employing a material that can be pierced by a syringe needle. For instance, means for sealing end 22 can be fabricated to include plastic film or a thin rubber insert, as known in the art, to allow access to interior region 18 via a hypodermic needle.

The size and wall thickness of tube 16 can vary depending on the sample being processes. Generally, the length tube 16 can be as small as about 1 centimeter and as large as about 12 centimeters with a diameter ranging from about 0.5 centimeters to about 3 centimeters.

Tube 16 includes porous support 34 at end 20. Porous support 34 deactivates a nucleic acid amplification inhibitor, as described above. In a specific embodiment of the apparatus, porous support 34 is a disk cut from IsoCode® chemically treated cotton matrix paper.

Porous support 34 has interior face 36 and outer face 38.

Porous support is held at end 20 of tube 16 by retaining means 40 and positioning means 42. In one embodiment, retaining means 40 is an O-ring fitted at end 20 of tube 16. Edge clamps and other suitable means also can be employed to fabricate retaining means 40.

Positioning means 42 can be a lip in the interior wall of tube 16, a cross bar connected to the interior walls of tube 16 or other means. Positioning means 42 are located near end 20 of tube 16 at a distance suitable to accommodate the thickness of porous support 34 and any other inserts, further discussed below.

Optionally, mesh 44 is positioned at outer face 38 of porous support 34. Mesh 44 can be, for example, woven from strands of nylon, polypropylene, fluorocarbon, polyester, stainless steel or other metal. In a specific embodiment of the apparatus, mesh 44 is made of nylon and is 40 ÿm pore size. Mesh 44 can retain solid impurities away from porous support 34 and can add rigidity and abrasion resistance to a thin, flexible porous support, such as, for instance, chemically treated cotton cloth or paper.

Optional desalting membrane 46 is positioned at interior face 36 of porous support 34. Desalting membrane 46 is fabricated from a material that retains ionic salt components, including, but not limited to, guanidine thiocyanate, magnesium ions, iron ions and others, as known in the art. Examples of suitable desalting membranes include, but are not limited to Sephadex/glass fiber composites, cation exchange membranes, and anion exchange membranes. More than one desalting membrane can be stacked in tube 16, onto interior face 36 of porous support 34.

Optional compression barrier 48 can be inserted between positioning means 42 and, either optional desalting membrane 46, or interior face 36 of porous support 34. Compression barrier 48 preferably is constructed from a plastic, incompressible material such as Teflon® polytetrafluoroethylene, rubber, polypropylene, polyethylene, and others. Compression barrier 48 has channels 50. Compression barrier 48 provides support for inserts at opening 20 and improves uniformity of the eluate volume removed from the porous substrate during flow through. In some embodiments, compression barrier 48 also causes the porous substrate to project outwards from the barrel of tube 16, thereby providing better contact between porous support 34 and a solid sample that is deposited on a solid substrate.

Figure 1B:
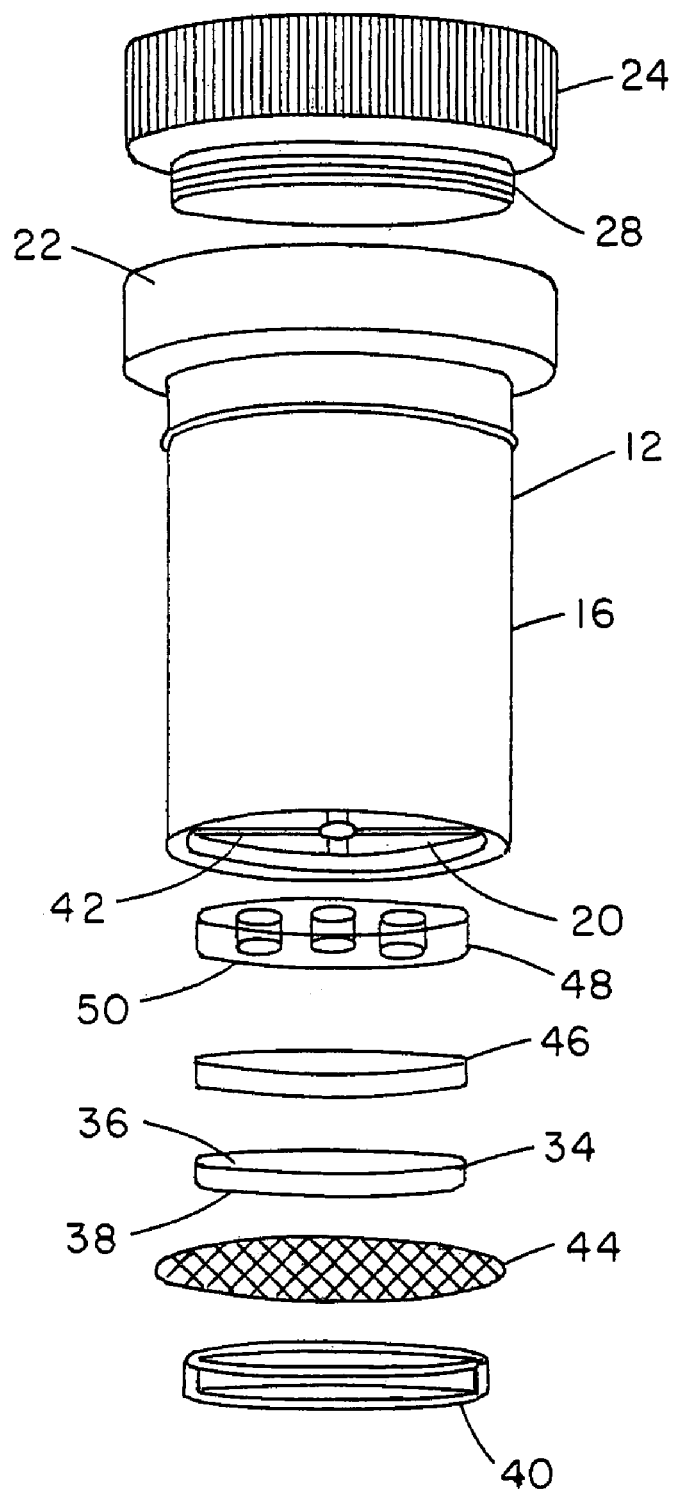
FIG. 1B is an exploded perspective view of a housing, cap, porous support and other elements that can be employed in one embodiment of the apparatus of the invention.

A side view of cap 24, tube 16, positioning means 42, compression barrier 48, desalting membrane 46, porous support 34, mesh 44 and retaining means 40 is shown in FIG. 1B.

Container 14 (shown in FIG. 1A) generally has a shape that conforms with the exterior surface of housing 12, such that when housing 12 is inserted into container 14, liquid present in container 14 is caused to flow through the porous support 34 and any other inserts.

Optionally, assembly 10 can be provided with means for applying an electric field, to enhance release of charged nucleic acids, held by porous support 34. In one embodiment, electrodes are positioned, respectively, at the end of bulb 32 and above mesh 44. In another embodiment, electrodes are embedded in positioning means 42 and mesh 44. Mesh 44 and positioning means 42 can be fabricated from of a conductive material, such as a metal, coated with a biologically-inert substance nonadherent to DNA. Contact to positioning means 42 can be made by means of a conductive material path embedded in the wall of tube 16 and leading from positioning means 42 to the outer walls of assembly 10. Generally, the electrode having a charge opposite that of a nucleic acid is positioned to attract the nucleic acid away from porous support 34 and towards interior region 18 of tube 16. Both electrodes can be connected to a DC power supply, as known in the art.

During operation, a raw sample, e.g., a solid, slurry, liquid or gas sample is contacted with porous support 34, optionally through mesh 44. The sample remains in contact with the porous support for a short interval, e.g., a few minutes. The sample also can be archived for processing at a later time, by storing housing 12 after the sample has been applied to porous support 34. Housing 12 is then inserted into container 14 which preferably encloses a suitable amount (e.g., about 2 milliliters to about 100 microliters (μl) in the case of a small, portable assembly 10) of the fluid reagent employed, e.g., water or water and buffer compounds, such that end 20 of tube 16 faces bottom 52 of container 14. Housing 12 is pressed towards bottom 52 of container 14, thereby forcing the fluid reagent through porous support 34 and optionally through desalting membrane 46, and any other inserts, to interior region 18 of tube 16. The nucleic acid component is eluted together with the flow-through fluid, to interior region 18 of tube 16, and is ready for amplification. It can be removed from housing 12 by dropper 30 or by other means, e.g. syringe. The nucleic acid component also can be stored or archived in the eluted fluid in assembly 10. Thus, the sample or the nucleic acid component can be processed immediately or can be stored in a suitable location, for a desired time period, for instance, for years or decades.

Figure 2A:
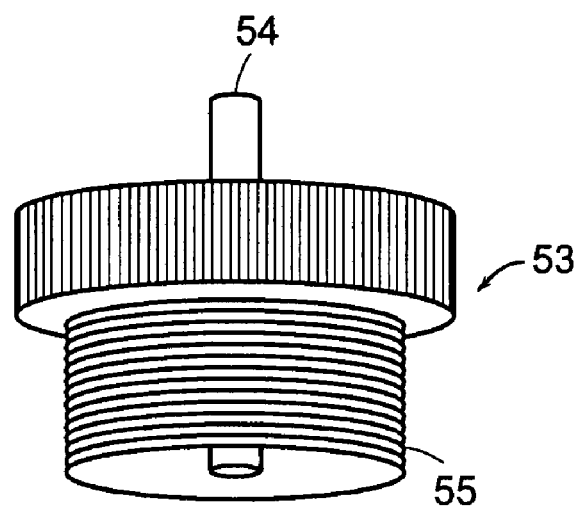
FIGS. 2A and 2B are side views, respectively of a cap and housing that can be employed in one embodiment of the apparatus of the invention.

In another embodiment of the invention, liquid is dispensed, in a metered fashion, to a housing such as described above. Side views of a cap and housing that can be employed are shown, respectively, in FIGS. 2A and 2B. Shown in FIG. 2A, is dispensing cap 53 which is provided with through hole 54 and threads 55. Preferably, a narrow through hole is employed.

Figure 2B:
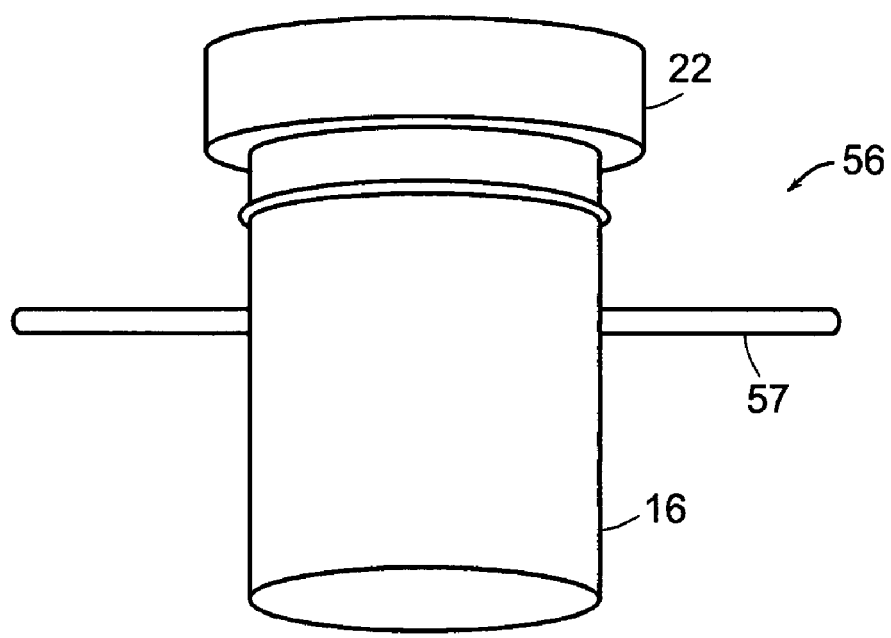

Threads 55 are matched to threaded grooves at end 22 of housing 56, the side view of which is shown in FIG. 2B. Housing 56, is essentially as described with respect to housing 12 in FIGS. 1A and 1B and has optional fins 57. Fins 57 serve to facilitate handling of housing 56 during sample application to porous support 34 and during operation when pushing housing 56 into a container such as container 14 shown in FIG. 1A.

Optionally, the exterior region of end 22 of housing 56 is provided with indentations or other markings for estimating fractions of a turn when dispensing cap 53 is rotated with respect to housing 56.

During operation, housing 56 is employed in conjunction with a container such as container 14 described above, with respect to FIG. 1A. Liquid is forced out of housing 56 by screwing in the cap, thereby displacing the liquid from the interior of housing 56 via through hole 54. In one embodiment, threads 55 are spaced such that a turn of a known angle displaces a known quantity of liquid out of the housing. In other embodiments, amounts of liquid removed can be measured for different rotation arcs to generate calibration charts.

In one embodiment of the invention, a nucleic acid component prepared as described above is further processed, e.g., by PCR procedures, as known in the art. For instance multiple samples can be collected and processed using multiple assemblies 10 each as described above. A manual press can be employed to process, for example, six assemblies at a time. An automatic press, e.g. COTS Whatman Mini-Uniprep Processor model #PR0000040, can be employed to process, for instance a batch of thirty assemblies. Signal analysis and procedures by which nucleic acids and organism from which they originate are identified also are known in the art.

Another embodiment of an apparatus for preparing a nucleic acid component for amplification includes cartridge 60 which includes a plurality of wells. Cartridge 60 and its operation are further described with respect to FIGS. 3, 4 and 5.

Figure 3:
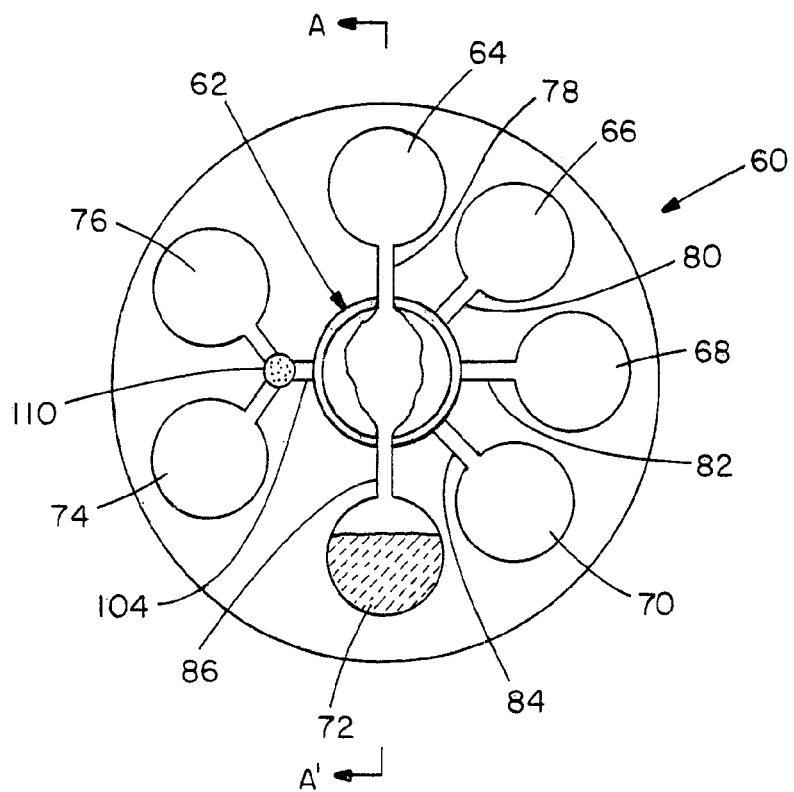
FIG. 3 is horizontal cross sectional view of an apparatus that can be employed to prepare a nucleic acid component in a sample for amplification.
Figure 4:
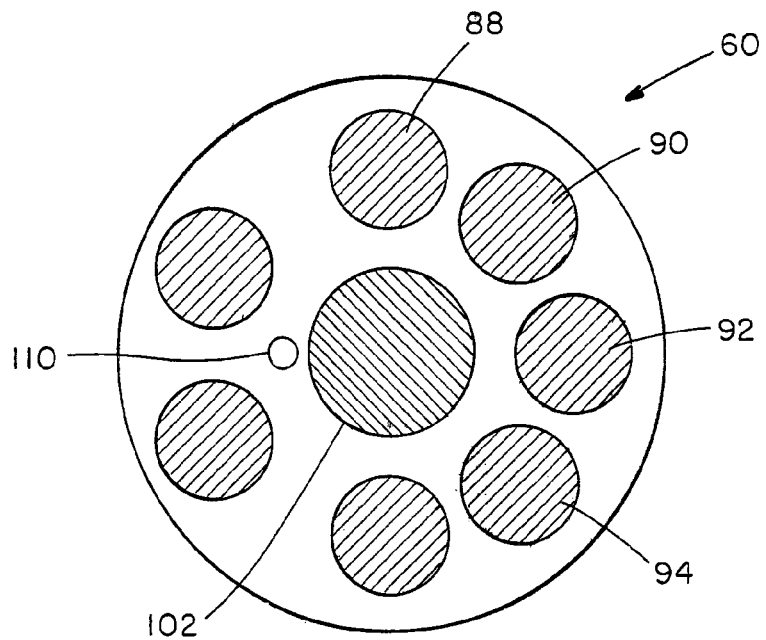
FIG. 4 is a top view of the apparatus of the invention in FIG. 3.
Figure 5:
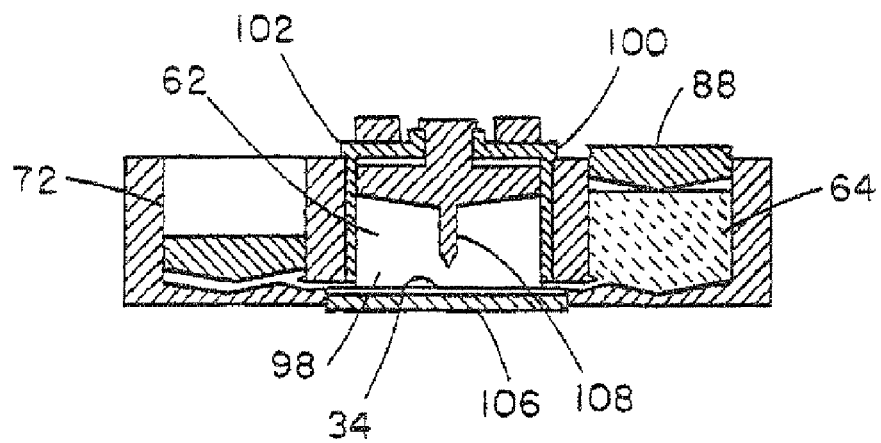
FIG. 5 is a cross sectional view along cutaway line $AA^1$ in FIG. 3.

Specifically, a horizontal cross sectional view of cartridge 60 is shown in FIG. 3, a top view, in FIG. 4 and a cross sectional view along cutaway line AA' of FIG. 3, in FIG. 5.

Cartridge 60 can be fabricated from a suitable material, preferably a plastic material, such as for example, polycarbonate, nylon, polydialkylsiloxanes, polyethylene or polypropylene terephthalates, polytetrafluoroethylene and others. Cartridge 60 also can be fabricated, in whole or in part, from glass or a metal such as steel, aluminum and other materials. Preferably, cartridge 60 is fabricated for a single use. Cartridge 60 has dimensions in the range of from about 5 centimeters to about 10 centimeters. Cartridge 60 includes a plurality of wells, specifically sample well 62 and chambers 64, 66, 68, 70, 72, 74 and 76. Generally, all the chambers are completely encapsulated in cartridge 60. In the embodiment shown in FIGS. 3 and 4, chambers 64, 66, 68, 70, 72, 74, 76 are arranged around sample well 62. Other arrangements of the chambers with respect to sample well 62 also can be employed.

Input chambers 64, 66, 68, 70 store reagents that are delivered to sample well 62. For example, chamber 64 stores wash water, chamber 66, elution water, chamber 68, buffer and chamber 70, reagent. Reagents and/or buffers can be stored in liquid form or can be stored in dry form and solubilized by adding water from additional input reservoirs (not shown in FIG. 3, 4 or 5) immediately prior to use. Preferably all reagents or fluids necessary to prepare a nucleic acid component in the sample for amplification are preloaded in cartridge 60 during manufacturing.

Output chambers 72, 74, 76 include collection chambers 74 and 76 (for product and waste, respectively) and used wash water receptacle 72. Depending on a particular sample and protocol, not all chambers shown in FIGS. 3 and 4 need to be employed.

Conduits 78, 80, 82 and 84, extend, respectively, from input chambers 64, 66, 68 and 70, to sample well 62. Sample well 62 can be provided with ports that are alignable with conduits 78, 80, 82 and 84.

Cartridge 60 is provided with means for selective communication between an input chamber and sample well 62. For example, selective communication can be achieved using a rotatable wall with one or more openings that align openings in sample well 62 with conduits to the other reagent chambers. In a preferred embodiment, the rotatable wall has two openings that align so that wash water can be introduced in sample well 62 and can exit sample well 62, via conduit 86, to wash water receptacle 72. Receptacle 72 can enclose a superabsorbent or a gel-like material that prevent subsequent leakage or spillage of wash water.

Other suitable means for providing selective communication between a chamber and sample well 62 include, slots or pins that can be manipulated manually or automatically. Input chamber 64, 66, 68 and 70, for example, can be constructed so that a wall area at conduits 78, 80, 82 and 84, respectively, bursts under pressure or if punctured, thereby providing selective fluid communication between each chamber 64, 66, 68 or 70 and sample well 62. In another example, fluid stored in a chamber can be expelled into sample well 62 by pressurizing the roof of the chamber, which includes an elastic membrane. Pressurizing results in the breakage of a seal membrane on the wall of the sample well. The base of each input chamber is shaped to result in complete expulsion of the fluid, as the elastic membrane is pressed down. Plungers 88, 90, 92 and 94 (shown in FIG. 4) also can be depressed to expel a fluid from any of chambers 64, 66, 68 or 70, as shown in FIG. 5 for chamber 64.

Sample well 62 can have any suitable dimensions. In one example, sample well 62 is sized to receive a fluid sample of up to about 5 ml.

In the interior of sample well 62, wall surfaces can be partially coated with a hydrophobic coating to enhance confining the sample and water-based reagents to the lower section of the well. Similar hydrophobic coatings can be provided to any of the other chambers in cartridge 60.

As seen in FIG. 5, sample well 62 includes porous support 34 that deactivates a nucleic acid amplification inhibitor, e.g., an insert of IsoCode® chemically treated cotton matrix paper. Porous support 34 is placed at lower end 98 of sample well 62.

Upper end 100 of sample well 62 is covered or sealed. In the embodiment shown in FIG. 4, sample well 62 is covered by lid 102 that includes an embedded gas-permeable membrane. The lid can be sealed, for instance, by a snap closure and an O-ring gasket. The gas-permeable membrane allows venting of vapors, e.g., water vapors generated during a heating step to dry a sample deposited on the porous support. Other means for sealing sample well 62 or for allowing venting of vapors also can be employed, as known in the art. For instance, sample well can be sealed with a cap provided with a relief valve.

Fluid communication also is established between sample well 62 and collection chambers 74 and 76, as seen in FIG. 3.

In one embodiment, collection chambers 74 and 76 are under vacuum. Pressure being applied onto fluid in sample well 62, for example by plunger means, or by applying force onto the gas-permeable membrane in lid 102, can cause rupture of a membrane closure at conduit 104. A membrane seal between sample well 62 and conduit 104 also can be ruptured by a pin puncture, effected manually or automatically. Contents in sample well 62 can thereby be emptied in collection chambers 74 or 76, as further described below.

During operation, a raw sample is introduced in sample well 62 and into contact with porous support 96 for instance through the hinged lid described above. No further access to cartridge 60 is necessary.

Selective fluid communication between sample well 62 and input chambers 64, 66, 68 and 70 is established in an order established by the protocol being used. Various reagents and fluid(s) are directed to sample well 62 and to porous support 96 via plungers or other suitable means, as discussed above.

The raw sample can be subjected to an electric field by electroelution electrodes 106 and 108. The electrodes are connected to a power supply, not shown in FIG. 5, of up to about 20V. Preferably, the electrode surfaces are treated to prevent attachment of nucleic acids. Electrode 108, at lid 102 can be flat or can have a pointed tip to provide electric field enhancement, as known in the art.

Heating also can be employed, alternatively or in combination with applying an electric field. Heating can be by external heating means or can be built into the cartridge design. In one example, thermoelectric heating can be employed. Thermo-electric heating can be employed using electrode 106. For many samples, heating, in the absence of an electric field, is for about 30 minutes at about 95° C.

Elution can include a concentration step in order to reduce the volume of the nucleic acid component. A binding matrix 110 is employed to retain nucleic acid while initial wash fluid is directed to collection chamber 76 (waste). Access to chamber 76 is then closed and nucleic acid is released from binding matrix 110 by introducing elution fluid, e.g., water, to elute bound nucleic acid from binding matrix 110 to collection chamber 74 (product).

Suitable materials that can be employed to form binding matrix 110 include, but are not limited to, silica or glass.

Furthermore, collection chambers 74 and 76 can be sealed by means of heat-sealable membranes, heated with pins, not shown in FIG. 3, 4 or 5. Thus product nucleic acid components can be stored in suspension in cartridge 60 or 120.

The sample also can be removed with a hypodermic needle that punctures cartridge 60 or 120, at a product withdrawal port, not shown in FIG. 3, 4 or 5.

Sample well 62 and chambers 64, 66, 68, 70, 72, 74 and 76 essentially as described above can be integrated with a nucleic acid hybridization, and optionally, amplification chambers.

Figure 6:
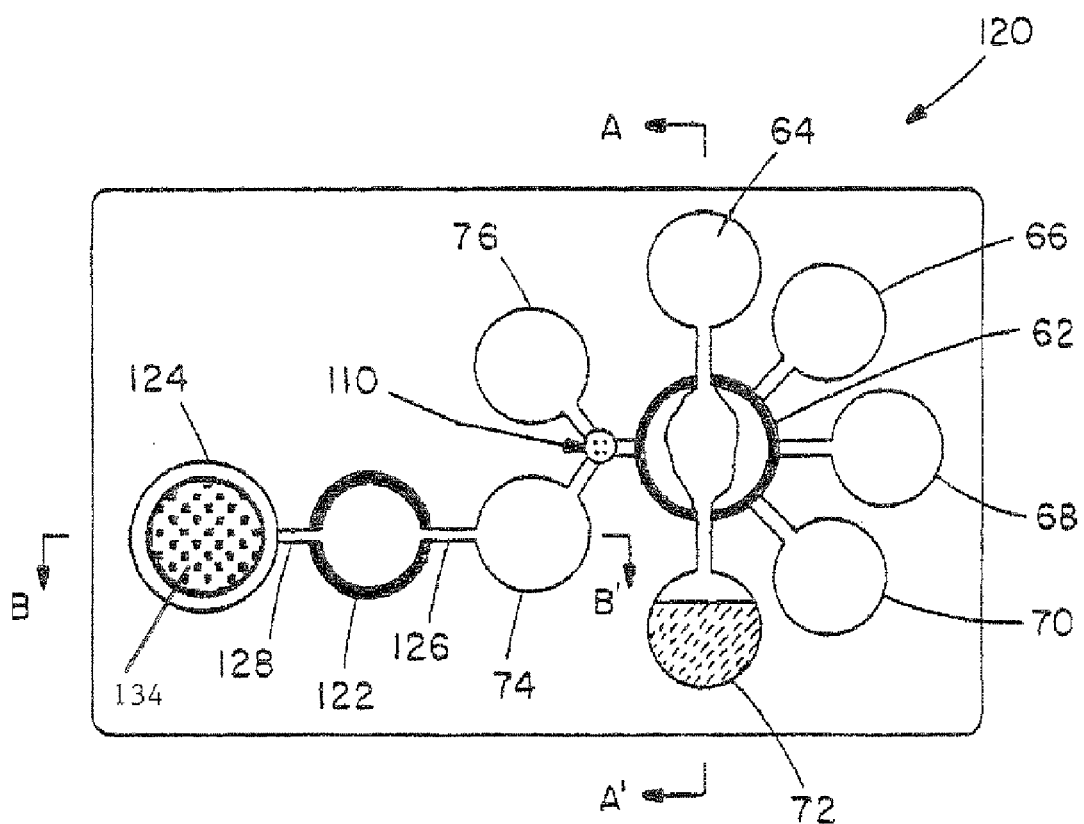
FIG. 6 is horizontal cross sectional view of an apparatus that can be employed to process a sample.
Figure 7:
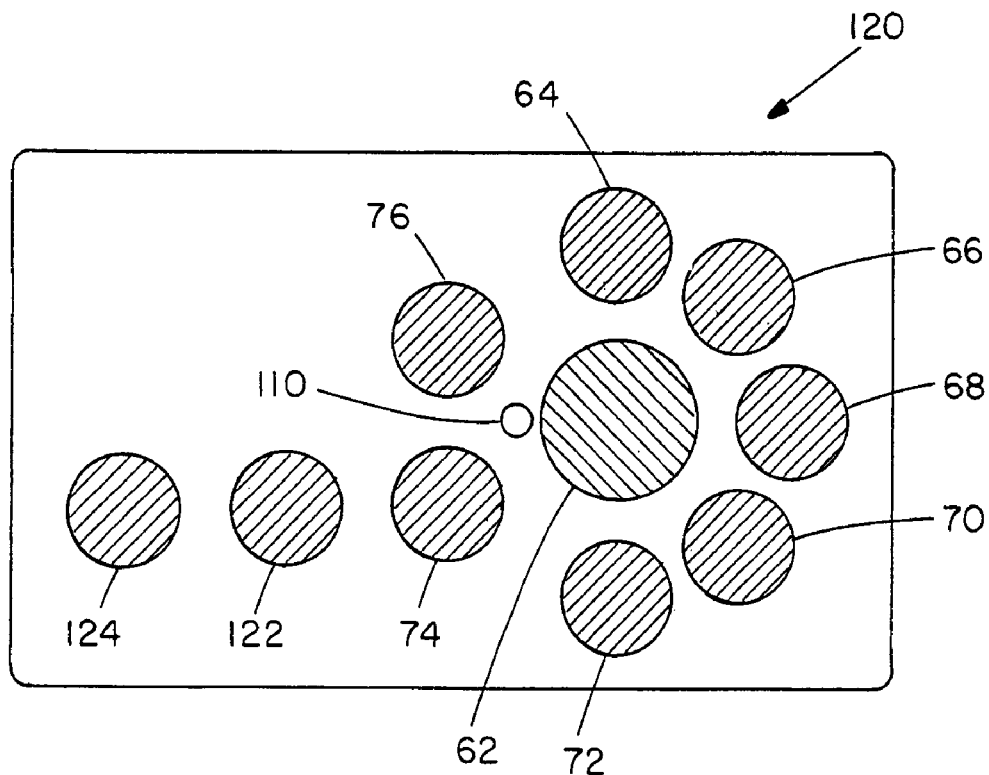
FIG. 7 is a top view of an embodiment of the apparatus in FIG. 6.
Figure 8:
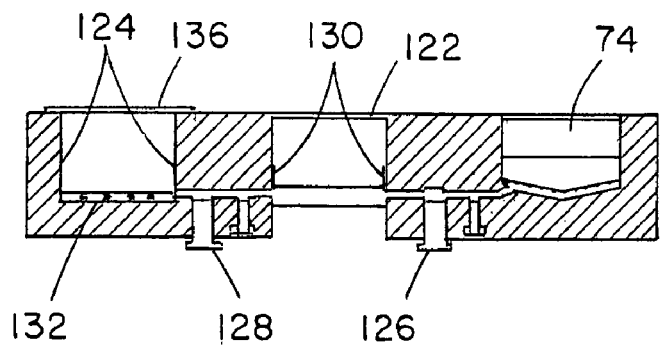
FIG. 8 is a cross-sectional view along cutaway line $BB^1$ in FIG. 6.

Integrated cartridge 120 is described with respect to FIGS. 6, 7 and 8.

In addition to the elements described above, integrated cartridge 120 includes amplification chamber 122 and hybridization chamber 124. Conduits for fluid communication are provided, respectively, for fluid communication between collection chamber 74, containing a nucleic acid component that is ready for amplification, to amplification chamber 122 and from amplification chamber 122 to hybridization chamber 124.

Nucleic acid amplification and hybridization procedures are known in the art.

Amplification chamber 122 receives the required primers and enzymes from a separate input reagent chamber (not shown), which can be pressure actuated as described above. Heat for the amplification reaction, if required, is supplied from an external source to the heater cavity, also not shown. Dry reagents 130 also can be provided. The chamber is prefabricated to be under vacuum, and accessed and sealed with heated pins 126 and 128 as described above. Hybridization chamber 124 contains array 132 of DNA/RNA printed on the base of the chamber. The interior walls of chamber 124 are coated with colorimetrically or fluorescently labeled oligonucleotide probes 134 (FIG. 6) which dissolve when hydrated and are used to detect hybridization. Alternatively, the probes and other reagents can be provided in the form of dried beads containing the reagents, which are rehydrated and dissolve when the fluid sample from collection chamber 74 is introduced into the hybridization chamber 124. The chamber has lid 136 fabricated from a transparent membrane, to allow observation of the array.

In a further embodiment, the invention is related to an apparatus for handling a raw sample such as, for instance, a soil sample, collected from the field. By employing the apparatus, raw sample components can be separated from the sample, which is then used, essentially as described above, to prepare an amino acid component of the sample for amplification.

Figure 9:
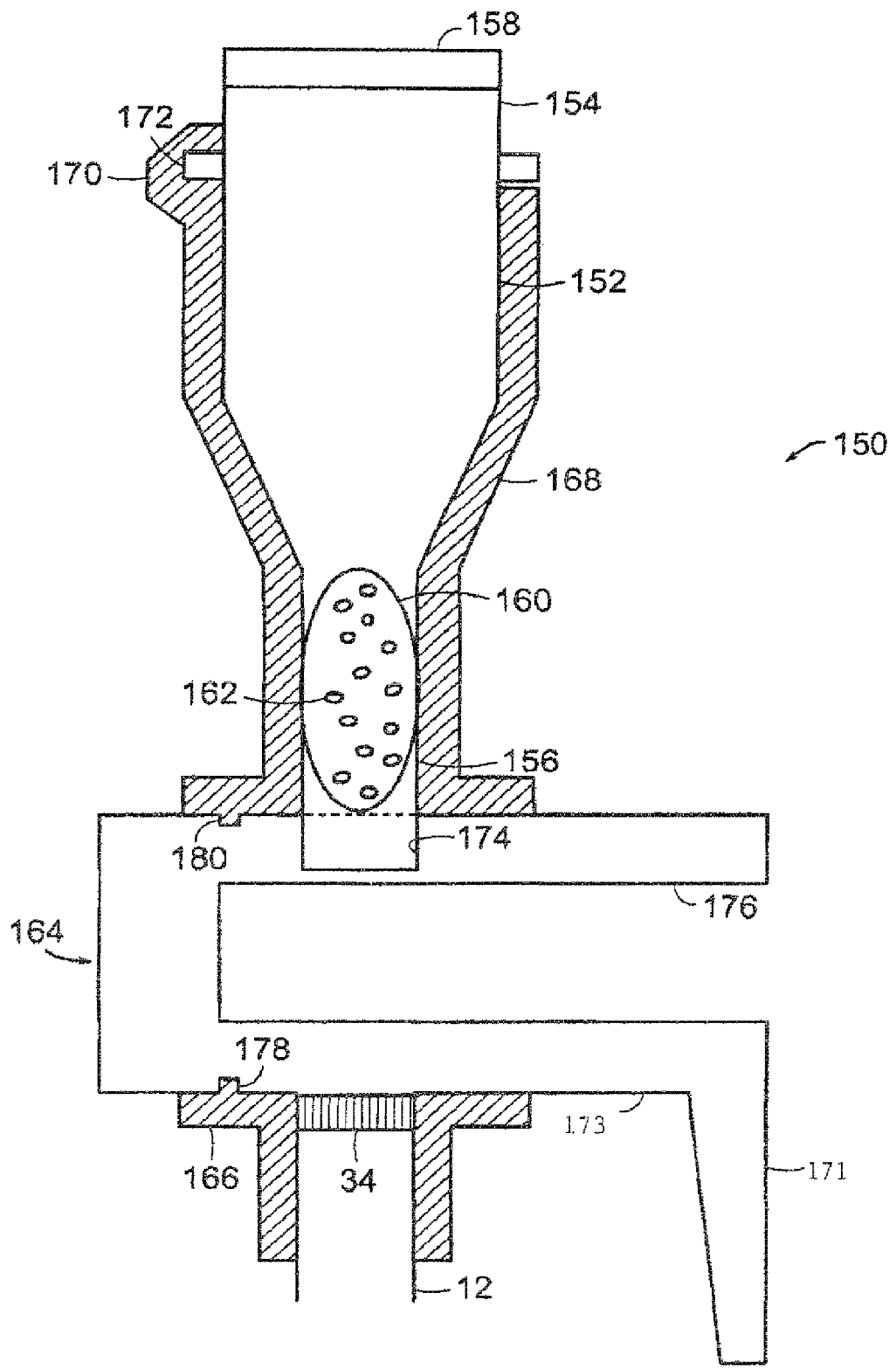
FIGS. 9, 10 and 11 are illustrations of an embodiment of an apparatus of the invention and its operation.

One embodiment of an apparatus of the invention is shown in FIG. 9. Shown in FIG. 9 is apparatus 150 which includes housing 12 and vessel 152. Housing 12 is essentially as described with respect to FIGS. 1A and 1B, or 2A and 2B, and includes porous support 34. Other means for processing the sample, as described above, for example, with respect to FIGS. 3-8 can be employed.

Vessel 152 can have any suitable shape and dimensions and can be constructed from metal, glass, plastic or other suitable materials. Preferably, vessel 152 is fabricated from plastic and has a length in the range of from about 5 centimeters (cm) to about 20 cm, more preferably in the range of from about 10 cm and about 15 cm. Vessel 152 preferably has a smallest diameter in the range of from about 2 cm and about 5 cm and a largest diameter in the range of from about 3 cm to about 8 cm.

Vessel 152 has inlet 154, provided with closure 158, and outlet 156. Closure 158 is, for example, a lid, cap, a rubber insert or other means for closing or sealing inlet 154. In one embodiment, closure 158 includes a flexible layer that can be ruptured by pressing. Closure 158 preferably is leak free with respect to materials, e.g., liquid, present in vessel 152. Vessel 152 houses ampoule 160 which contains magnetic beads 162, essentially as described above. In one embodiment, magnetic beads 162 are stored in buffer within ampoule 160. Ampoule 160 preferably is fabricated from a material that can be pierced or torn by a plunger, for example by a plunger that can be depressed through closure 158.

Ampoule 160 can be supported by positioning means such as indentations or ribs constructed in the vessel walls, or by other suitable means. In one embodiment, the ampoule is held in vessel 152 near inlet 154, by suitable positioning means, e.g, a supporting ring in the walls of vessel 152. In another embodiment, the ampoule is formed as a chamber within closure 158, which is, for example, a threaded cap. Magnetic beads 162 are held in the chamber by a rupturable membrane that can be punctured by twisting or turning closure 158. Closure 158 also can be provided with a plunger or other mechanism for puncturing the rupturable membrane or ampoule wall to release the beads.

Both housing 12 and vessel 152 are secured to rotatable valve 164, for example through supports 166 and 168, respectively. Optionally, support 168 has snap closure 170 for engaging over optional lip 172 of vessel 152. A similar arrangement also can be employed with respect to support 166 and housing 12.

Rotatable valve 164 includes handle 171 and valve body 173, Valve body 173 is provided with well 174 for receiving magnetic beads 162, and recess 176. In one embodiment, rotatable valve 164 has a grove for engaging, during rotation, lip 178 at bracket 166 and lip 180 at bracket 168.

During operation, a raw sample is introduced in vessel 152 through inlet 154. Water, buffer or another solvent also can be added. The contents of ampoule 160 are released from ampoule 160 by means such as discussed above and magnetic beads 162 are brought into contact with the raw sample. In a preferred embodiment, magnetic beads 162 have a coating such that the sample that includes a nucleic acid component is preferentially captured by or attached to magnetic beads 162. Shaking or stirring is optionally provided, for example to enhance contact and adherence of sample components onto the beads. Manual shaking or other means of agitation can be employed, as known in the art.

Figure 10:
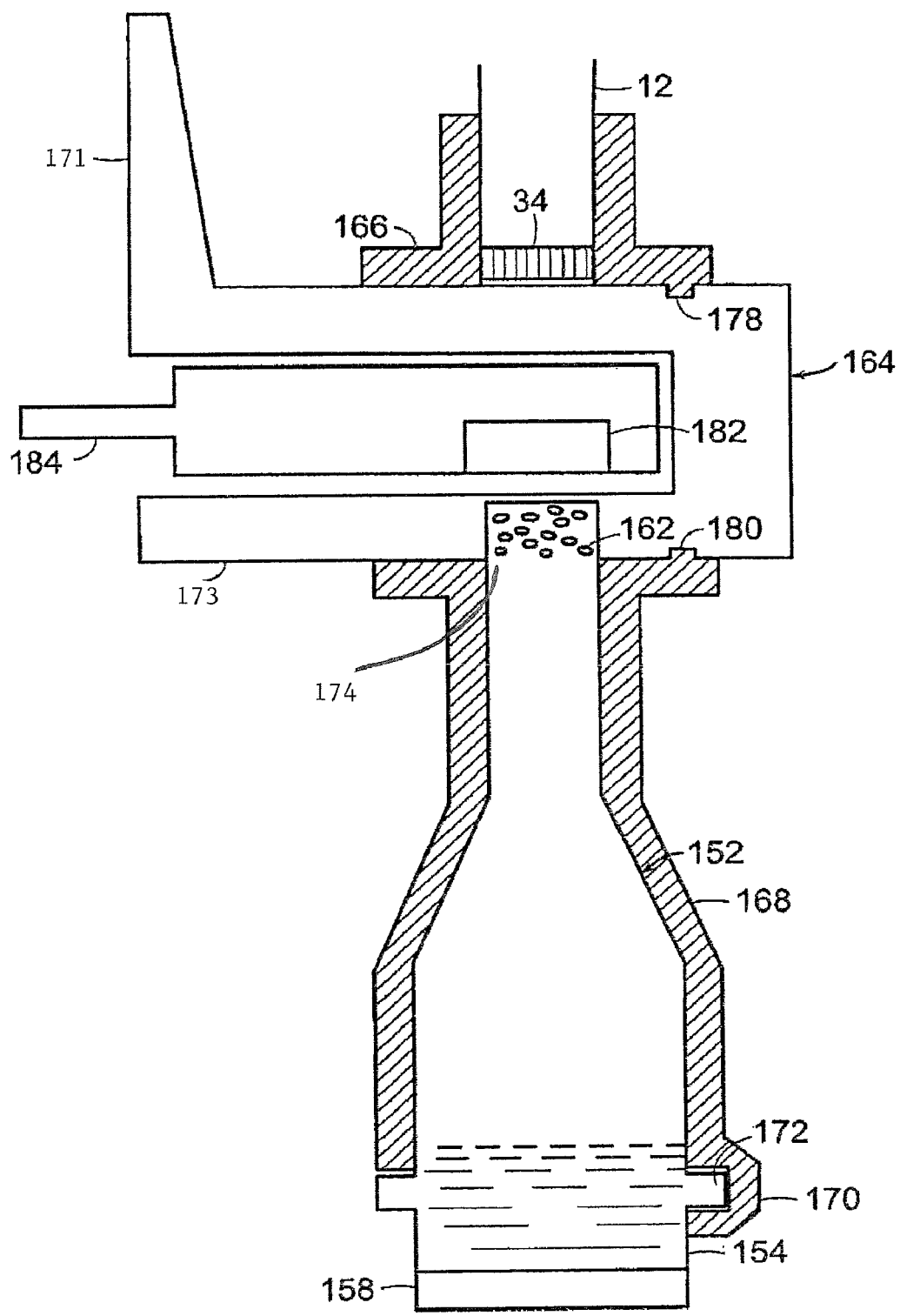

Shown in FIG. 10, is inverted apparatus 150. Magnet 182, e.g., a rare earth magnet, held in magnet handle 184 is placed in recess 176. As shown in FIG. 10, magnetic beads 162 migrate upwards towards magnet 182 and preferably gather in well 174, thereby separating a sample from raw sample components. The arrangement shown in FIG. 10 also takes advantage of the gravitational force on raw components such as debris, soil particles, sand and other materials that can undergo sedimentation towards inlet 154 of vessel 152.

Figure 11:
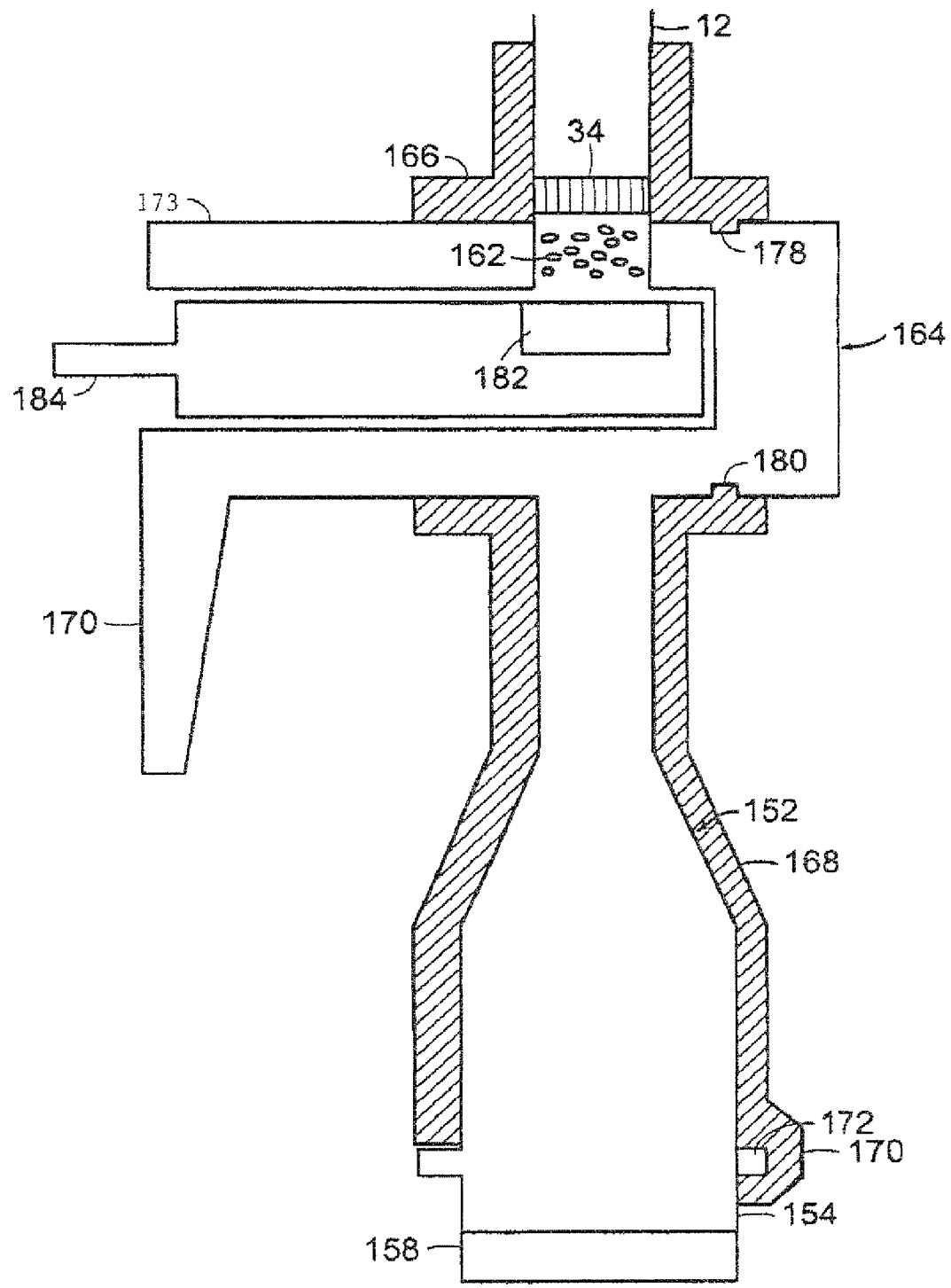

Rotatable valve 164 is then rotated, for instance by turning handle 171, to the arrangement shown in FIG. 11. As shown in FIG. 11, the rotation deposits the sample collected on magnetic beads 162, held by magnet 182 in well 174, at porous support 34 of housing 12. The sample is then processed as described above, for example with respect to FIGS. 1A and 1B. Embodiments related to methods and apparatus for further processing the sample also are described in U.S. application Ser. No. 10/193,742, titled Apparatus and Method for Isolating a Nucleic Acid From a Sample, filed on Jul. 10, 2002, the entire teachings of which are incorporated herein by reference.

Another embodiment of the apparatus of the invention is shown in FIGS. 12, 13A, 13B and 13C.

Figure 12:
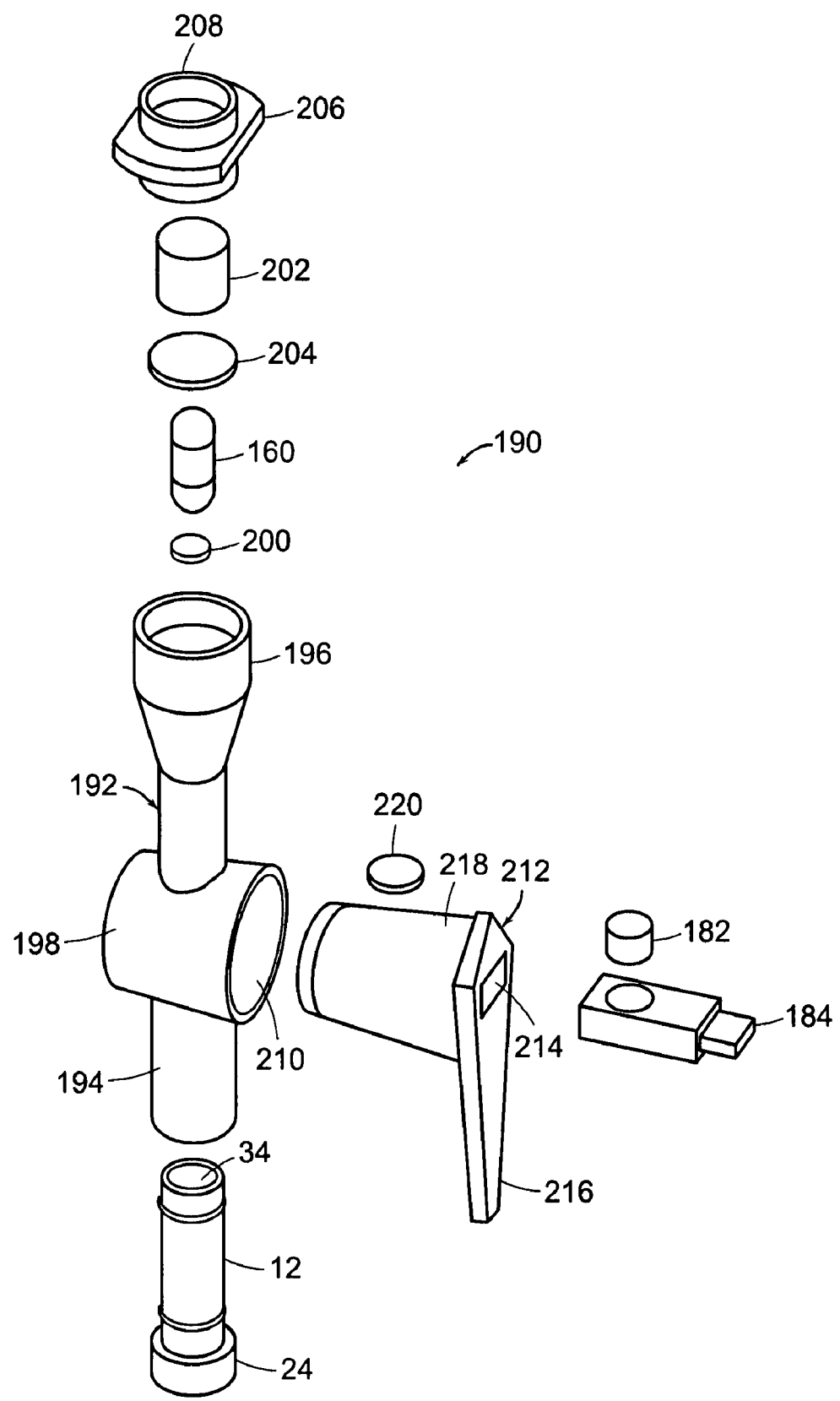
FIG. 12 is an exploded side view of another embodiment of the apparatus of the invention.

Shown in FIG. 12 is an exploded side view of apparatus 190 having main body 192. Main body 192 includes container 194, vessel 196 and region 198. Container 194 holds housing 12, which includes porous support 34, essentially as described above. In a preferred embodiment, housing 12 has cap 24 which includes a septum type closure for withdrawing liquid by a hypodermic needle. Preferably, container 194 performs the function of container 14, described in FIG. 1A.

Vessel 196 houses ampoule 160, which contains magnetic beads, as described above. Optional screen 200 is provided below ampoule 160 to prevent raw sample debris from being collected and transferred to porous support 34 of housing 12.

Vessel 196 also includes waste gel 202 which can released by rupturing separating layer 204, preferably made from a rupturable film or plastic. Gel 202 can be a silica gel, a clay, another desiccant or other absorbing materials and can be released to absorb liquid in the raw sample, if so desired. For example, waste gel 202 can be released prior to transporting a liquid or slurry raw sample in vessel 196. In one embodiment, waste gel 202 is held in a plastic pouch. The pouch and/or separating layer 204 can be ruptured, for instance, by tightening or pressing down cap 206, by twisting or by a plunger mechanism. Cap 206 can be provided with raised wall 208, which protects the upper end of the plastic pouch housing waste gel 202.

Main body 192 also includes region 198 which has opening 210 for holding rotatable valve 212. Rotatable valve 212 has recess 214 for receiving magnet handle 184, which holds magnet 182, essentially as described above. A thin plastic layer can be provided to protect magnet 182 from being contaminated by sample components. For example, the protective layer can be part of rotating valve 212 or it can be a cover of magnet 182. Rotatable valve 212 includes handle 216 and is provided with well 218. Bag 220 includes a fluid reagent, e.g., water, buffer, TAE, TBE, and is inserted in well 218.

Figure 13A:
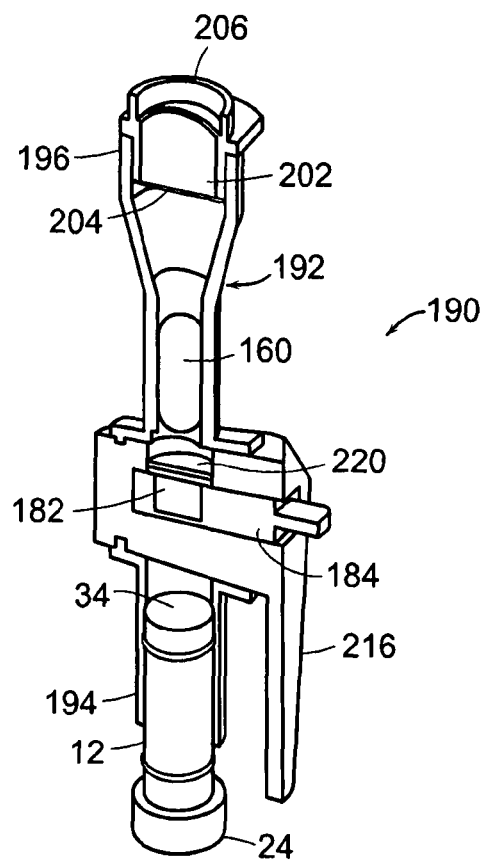
FIG. 13A is a longitudinal cross-sectional view of the apparatus shown in FIG. 12.
Figure 13B:
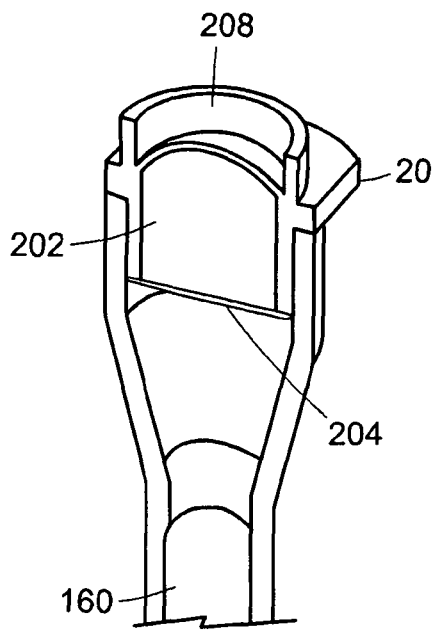
FIGS. 13B and 13C are enlarged cross-sectional views of portions of the apparatus shown in FIGS. 12 and 13A.
Figure 13C:
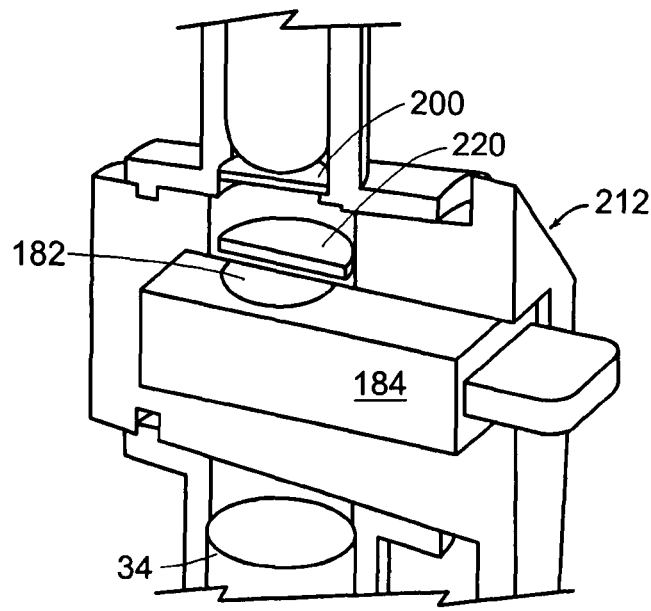

A side cross-sectional view of apparatus 190 is shown in FIG. 13A. Shown in FIG. 13B is a close-up cross-sectional view of the upper part of vessel 196, including layer 204, gel 202 and cap 206 having raised wall 208. Shown in FIG. 13C is a close-up cross-sectional view of rotating valve 212, magnet 182 in magnet handle 184, bag 220 and screen 200.

As described above, during operation, magnetic beads 162 are released and contacted with a raw sample in vessel 196, in the absence of magnet 182. Optional agitation can be employed to enhance contact and capture of the sample onto the beads. Magnet handle 184, with magnet 182 is inserted into opening 210 so that magnetic beads 162 are deposited in well 218. Optionally, gel 202 is released by rupturing layer 204. Rotating valve 212 is then turned and the sample collected on magnetic beads 162 is brought near porous support 34. Magnet 182 in magnet handle 184 can be withdrawn from recess 214 thereby depositing magnet beads at porous support 162. In another embodiment, magnetic beads 162 are brought in contact with porous support 34 while magnet 182 and magnet handle 184 are in recess 214. Pushing housing 12 towards well 218 breaks bag 220, thereby releasing fluid, e.g., buffer from bag 220. The fluid contacts the sample attached to the magnetic beads and is pushed through porous support 34, whereby the nucleic acid component in the sample is directed through the porous support and nucleic acid amplification inhibitors are deactivated by the porous support, essentially as described above.

Housing 12 also can be employed independently of the apparatus of the invention. For example, housing 12 can be detached from the apparatus described with respect to FIGS. 9-13 and a sample can be collected by swiping the porous support of the housing over the sample and processing the sample, as described in U.S. application Ser. No. 10/193,742, titled Apparatus and Method for Isolating a Nucleic Acid From a Sample, filed on Jul. 10, 2002, the entire teachings of which are incorporated herein by reference.

The sample can be processed in a multiple-cartridge cassette and/or an automated cartridge processor. Commercial units, such as, for example, a robotic handler available from Beckman Coulter, Fullerton, Calif., under the name of Beckman Sagian™ Core System, can be employed or modified to accommodate the sample.

The invention is further illustrated by the following examples which are not intended to be limiting.

EXEMPLIFICATION

Example 1

A general commercial method for using IsoCode® chemically treated cotton matrix paper includes the following steps:
Apply sample directly to IsoCode® chemically treated cotton matrix paper;
Dry via desiccation or baking;
Rinse by vortexing in deionized water ($dH_2O$);
Submerge rinsed IsoCode® a chemically treated cotton matrix paper in $dH_2O$ and heat at 95° C. for 30 minutes;
Pulse vortex to remove DNA from paper; and
DNA is ready for PCR amplification.

A detailed protocol for preparing a DNA component of a raw solid sample (preferred to as the matrix), that can be prepared into a slurry, for amplification by employing Iso- Code® chemically treated cotton matrix paper, in the absence of the invention, is shown as Comparative Protocol A.

Comparative Protocol A

1. Measure 50 mg of the matrix into aluminum weighing dish (or any hydrophobic, non-silica-based weighing container).
2. Place a triangle of IsoCode® a chemically treated cotton matrix paper into another clean weighing dish.
3. Add as much distilled water to the matrix as is needed to be able to remove 15 μL from the sample. This is usually 25-30 μL for sandy soils, 35-40 μL for finer-grained or clay-containing soils, and a variable amount for other matrices.
4. Mix the matrix and the water well with the pipette tip used to add the water to the sample, until a fairly uniform in slurry is formed. Pipette up and down if possible, to increase sample mixing. Use filter tips to minimize pipette contamination.
5. With the same pipette tip, extract approximately 15 μL of liquid from the slurry; this may have some amount of suspended solids in it.
6. Apply the liquid to IsoCode® chemically treated cotton matrix paper.
7. Bake IsoCode® chemically treated cotton matrix paper piece for a minimum of 15 minutes (or until totally dry) at 60° C. under vacuum, or let dry for a minimum of 4 hours with desiccant in a sealed container at room temperature.
8. Remove dried IsoCode® chemically treated cotton matrix paper pieces from oven, and for each sample prepare a 1.5-mL-tube with 500 μL of distilled water (wash tube) and a 0.5-mL-tube with 50 μL of distilled water (eluate tube). The eluate tubes need to be labeled with sample numbers, the wash tubes do not.
9. Without touching the piece of IsoCode® chemically treated cotton matrix paper, place it in the wash tube. Close the cap and vortex 2-3 times for 1 second each.
10. Uncap the tube, and using a clean pipette tip, remove the piece of IsoCode® chemically treated cotton matrix paper and place into the eluate tube, and close the tube. Make sure that the IsoCode® chemically treated cotton matrix paper is completely submerged and that there are no air bubbles in contact with it. Discard wash tube. Repeat with remaining samples, using a fresh pipette tip each time.
11. Using the thermocycler or heating block, heat all eluate tubes at 95° C. for 30 minutes. If the tubes cannot be postprocessed immediately after this step, cool them to 4° C. and hold.
12. When the tubes have cooled, remove them from the thermocycler and remove each piece of IsoCode® chemically treated cotton matrix paper from its tube, using a pipette tip to extract as much liquid as possible from the paper into the tube before discarding the paper. A fresh pipette tip is used for each sample.
13. The eluate is ready for PCR analysis.

Protocol B was developed to include the method of the invention for being conducted in an assembly such as assembly 10, described above and illustrated in FIG. 1A.

Protocol B

1. Apply sample to porous support (IsoCode® chemically treated cotton matrix paper), by dropping liquid sample on it or wiping surface to be sampled.
2. Wait 5 minutes.
3. Push water or buffer-containing water through porous support by inserting the housing of the assembly into the container which already encloses 100-200 microliters of the water or buffer-containing water.
4. Remove the eluate (water containing nucleic acid component of the sample) with a pipette tip after opening the housing of the assembly by removing the removable cap.

A comparison of the two protocols, Comparative Protocol A and Protocol B illustrate the reduced time and number of steps necessary to prepare a nucleic acid component for amplification when using the method of the invention and an embodiment of the apparatus of the invention. For example, both heating cycles have been eliminated. Elimination of the drying steps may be associated with a loss in the efficiency of extraction of nucleic acids from the sample, as it is believed that the initial drying step contributes to the binding of inhibitors to the porous substrate. Thus in some of its embodiments, the method of the invention optionally can include a single heating step. In other embodiments the method of the invention can employ electroelution, to enhance removal of the nucleic acid components from the porous support.

A modification of Protocol B, that also can be employed, provides additional contact time between the sample on the porous support and the water or buffer-containing water, prior to pushing the liquid through the porous support. This increases the efficiency of recovery of the nucleic acids.

Modified Protocol B

1. Apply sample to porous support (IsoCode® chemically treated cotton matrix paper), by dropping liquid sample on it or wiping surface to be sampled.
2. Wait 5 minutes.
3. Push the housing of the assembly into container, which already encloses 100-200 microliters of the water or buffer-containing water, until the porous support is in contact with the liquid in the container.
4. Wait 5-10 minutes.
5. Push water or buffer-containing water through porous support by fully pressing the housing of the assembly into the container.
4. Remove the eluate (water containing nucleic acid component of the sample) with a pipette tip after opening the housing of the assembly by removing the removable cap.

Materials and Methods for Examples 2, 3 and 4

PCR Amplification Procedures and Data Analysis

Data was obtained from a polymerase chain reaction (PCR) amplification procedure (hereafter referred to as Taq-Man™ gene expression assay performed on a series of DNA samples using the ABI PRISM® 7700 Sequence Detection System (part #7700-01-200/208, manufactured by Applied Biosystems, 850 Lincoln Centre Drive, Foster City, Calif., 94404).

The TaqMan™ gene expression assay system works by amplifying the DNA present in the sample with a "normal" PCR technique, while simultaneously monitoring the quantity of DNA being replicated in real time. This is accomplished as follows:

A normal PCR cycle starts. The DNA is denatured, and the probes for either end of the sequence to be replicated bind. At this point, a specialized probe also binds to the middle of the sequence. It is labeled with a fluorogenic "reporter" dye on one end, and a "quencher" on the other. When these two molecules are in close proximity (i.e. bound to the same strand of DNA) the fluorochrome is quenched by the quencher molecule and no light is given off.

Once the probes at either end of the sequence have bound, the DNA polymerase progresses along the DNA, making the single strand double stranded. When it reaches the fluorogenically labeled probe, its 5' nuclease activity cleaves the probe into separate bases as it progresses down the strand. This liberates the fluorophore, allowing it to move away from the quencher, and permitting it to fluoresce.

The TaqMan™ gene expression assay measures the fluorescence intensity inside the tube at each cycle and records it for analysis by the software. Each cycle doubles the number of DNA strands with the correct sequence, and the corresponding fluorescent signal being recorded by the TaqMan™ gene expression assay at the end of the cycle.

Data is shown in the form of a logarithmic-linear plot, with relative signal fluorescence level (Rn) on the y-axis and the amplification cycle number (Cycle) on the x-axis. A detection threshold is set by the user, and any signal exceeding the detection threshold level and following the exponential amplification curve shape shown in the plot is considered to be a "positive hit". The cycle number at which the detection threshold is exceeded is referred to as the cycle threshold for that particular sample. A lower cycle threshold indicates a larger starting quantity of DNA in the sample (all other factors in the sample being equal).

Description of Seeding Procedures Used

Vegetative bacterial cultures are prepared in bacterial growth medium, from frozen stocks of bacteria. Cultures are grown overnight, to late log phase growth stage, and typical cultures contain approximately $10^8$ cells/mL of growth medium. Dilutions of the stock culture used for seeding are prepared by volumetric dilution in a diluent of growth medium, or the liquid in which the sample is to be seeded. A typical dilution series consists of dilutions from 1:10 (bacterial culture:diluent) down to 1:10, by factors of 10. Samples are mixed by vortexing.

Example 2

Dry spores were collected from air onto a porous support in an assembly such as assembly 10, described above and shown in FIG. 1A.

A commercial mini vacuum cleaner, obtained from Microcenter, Cambridge Mass. was adapted to hold the assembly. The air stream was directed towards the porous support at one end of the assembly.

Once a sample was collected onto the porous support, nucleic acid component in the sample was prepared for amplification using Protocol B, steps 2 to 4, described in Example 1.

Figure 14:
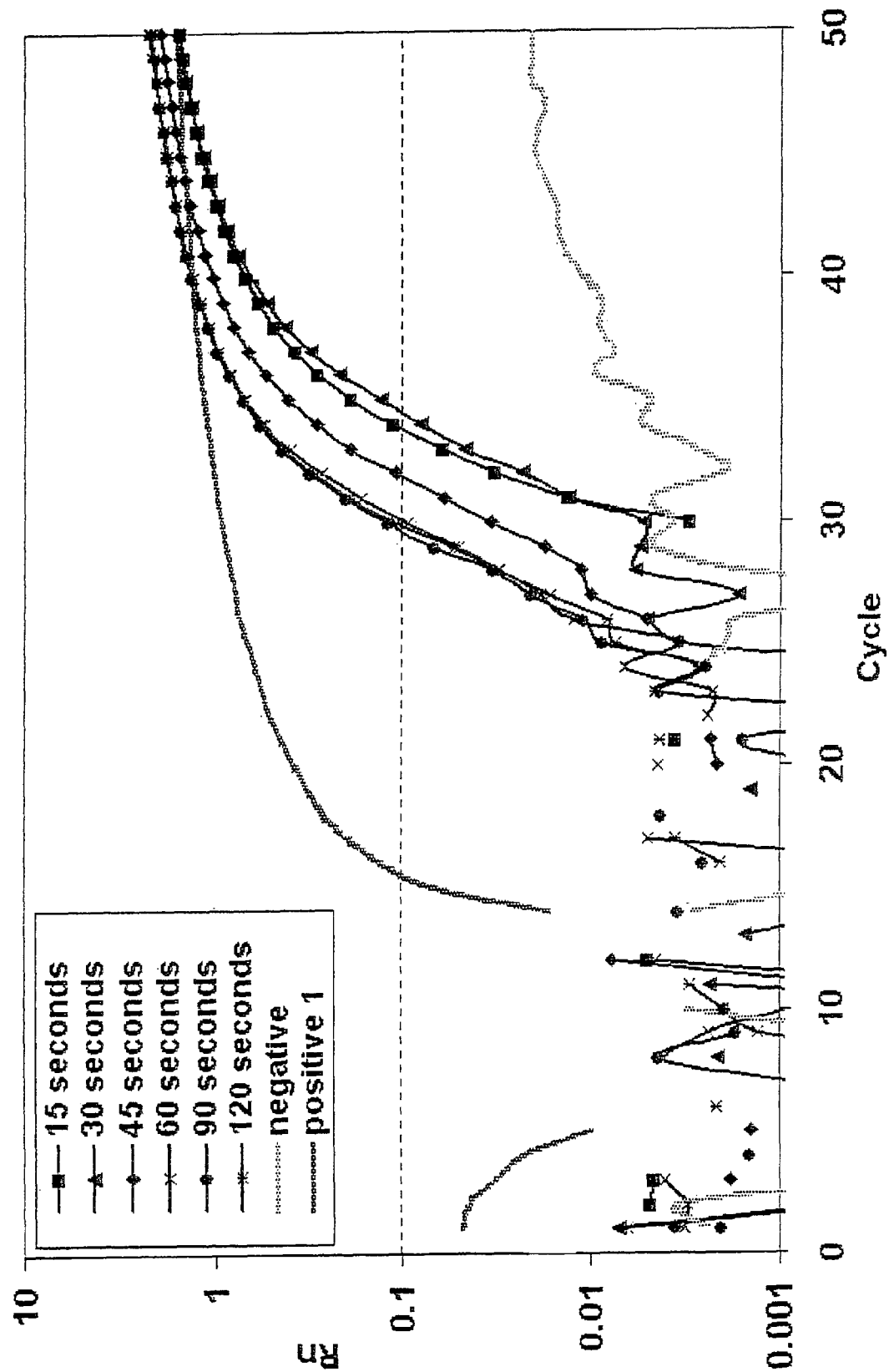
FIG. 14 presents a series of plots showing relative signal fluorescence level vs. amplification cycle number from air samples contacting a porous support according to the invention.

TaqMan™ gene expression assay amplification results for samples collected by air impaction for periods ranging from 15 seconds to 2 minutes are shown in FIG. 14. The results indicate that impaction times of as low as 15 seconds (translating to particle counts of thousands of particles per liter of air) were sufficient to detect and identify the target spore particles.

Example 3

Figure 15:
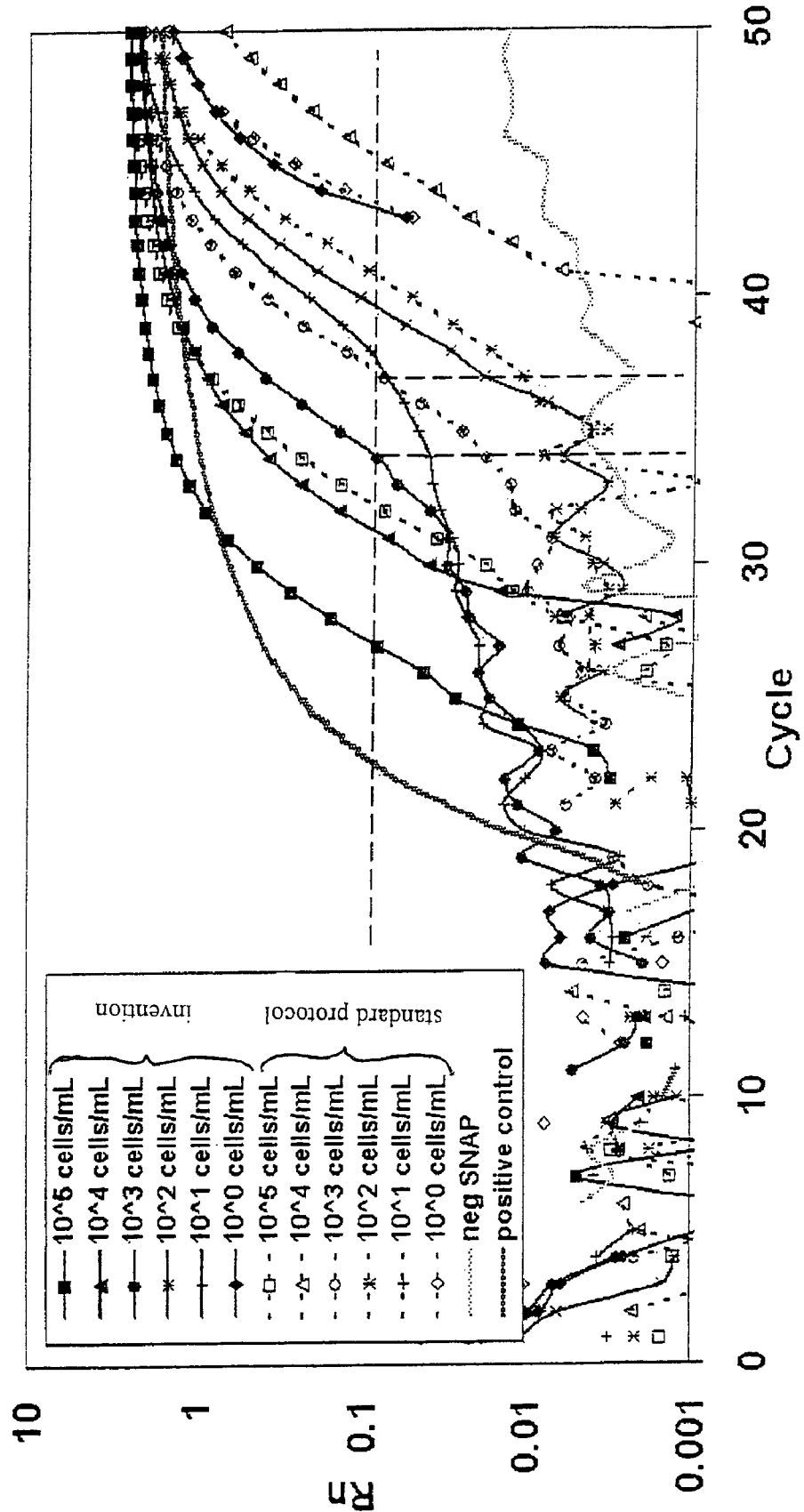
FIG. 15 presents a series of plots showing relative signal fluorescence level vs. amplification cycle number from various samples prepared by embodiments of the method and apparatus of the invention and by a comparative technique.

An assembly such as described above with respect to FIG. 1A was employed to prepare nucleic acid components of several samples for amplification. Samples were prepared by seeding dust contaminated water with bacterial cell cultures at various dilutions. Samples were processed using comparative protocol B, and the standard protocol given by the manufacturers of IsoCode® chemically treated cotton matrix paper. TacMan™ gene expression assay amplification results are shown in FIG. 15. Results indicate that reductions in cycle thresholds were obtained in all samples using the assembly described in FIG. 1A, as compared to identical samples processed using the standard protocol.

Example 4

Protocol C was developed to demonstrate the advantages of applying an electric field in conjunction with a porous support capable of deactivating a nucleic acid amplification compound in a sample. Protocol C was conducted with an electroelution device.

Figure 16:
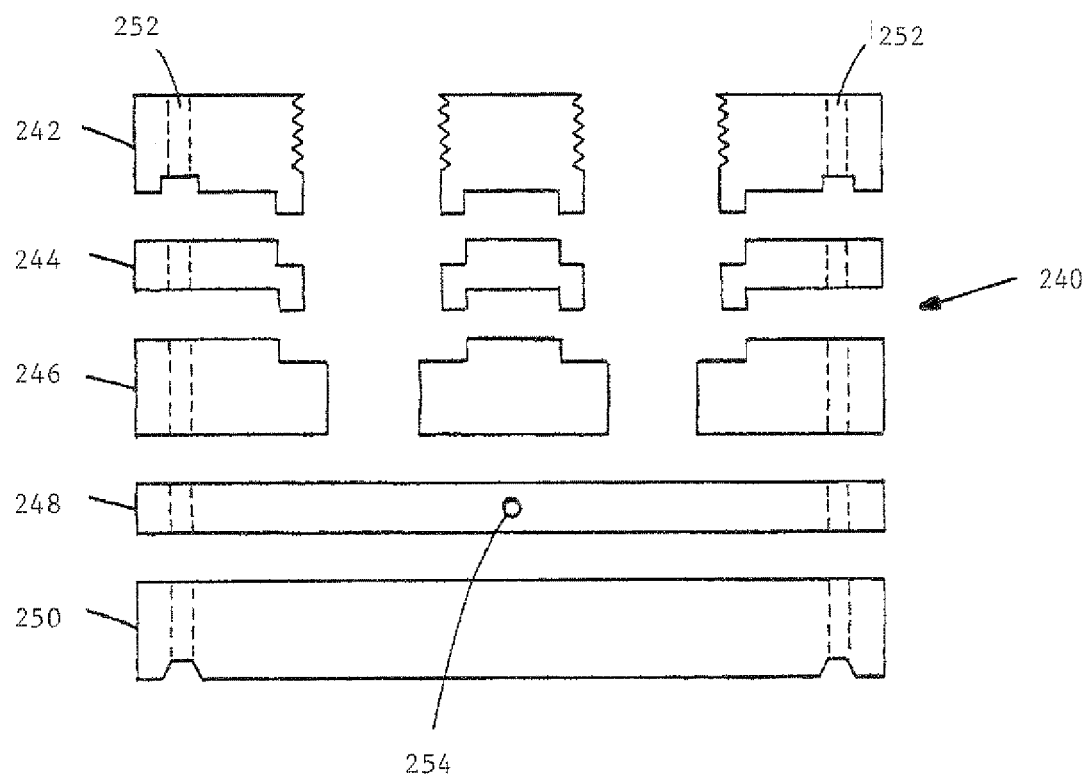
FIG. 16 is a cross-sectional view of an electroelution device for applying electric current to enhance removal of a nucleic acid from the porous support.

A cross-sectional side view of such a device, electroelution jig 240 is shown in FIG. 16. Electroelution jig 240 includes plates 242, 244, 246, 248 and 250 which can be assembled stacked upon each other by using screws and nuts through channels 252. Plates 242, 244, 246, and 250 are fabricated from a material such as Plexiglas, polycarbonate, or other inert material that does not adhere DNA. Plate 248 is fabricated from a conductive material such as a metal.

Figure 17:
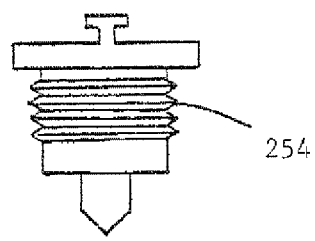
FIGS. 17 and 18, respectively, are cross-sectional and top views of an electrode employed in the device shown in FIG. 16.
Figure 18:
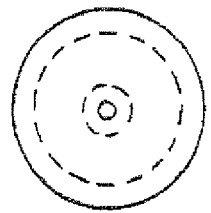
Figure 19:
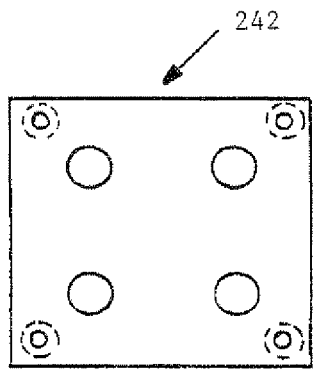
FIGS. 19-23 are top views of individual plates employed in the device shown in FIG. 16.
Figure 20:
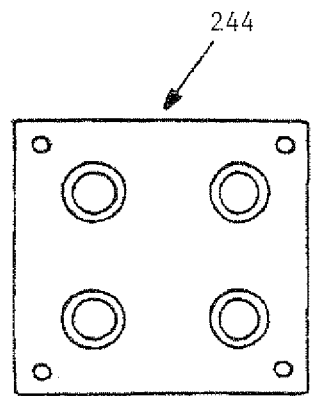
Figure 21:
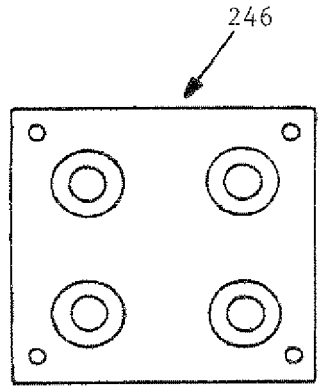
Figure 22:
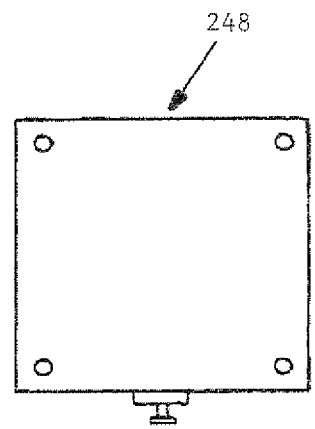
Figure 23:
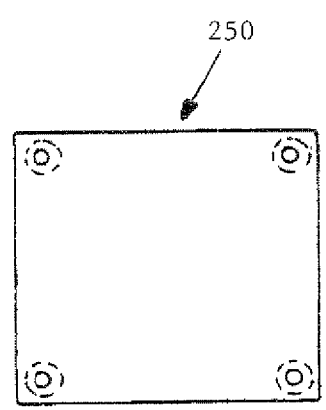

Plate 242 is threaded to receive 4 collection electrodes 254. Electrode 252 is fabricated from a conductive material such as a metal and preferably is in the shape of a threaded screw. A cross-sectional view and a top view of one electrode 254 are shown, respectively, in FIG. 17 and FIG. 18.

Top views of each of plates 242, 244, 246, 248 and 250 are shown, respectively, in FIGS. 19, 20, 21, 22 and 23. Voltage can be applied to plate 248 and electrode 254 from an external source, e.g., DC battery, not shown in FIG. 20. Preferably, plate 248 is the negative electrode and electrodes 254 are positive. In jig 240 a porous support, e.g., IsoCode® chemically treated cotton matrix paper, can be placed in the wells created by plate 246, or can be clamped between plates 246 and 248 (the negative electrode). Size-exclusion filters (e.g. 100 Daltons (Da) size) of a size to exclude all particles except the nucleic acid component of the sample, can be clamped between plates 244 and 246 and between plates 242 and 244 to permit the eluted DNA to pass to electrode 254 (the positive electrode).

Protocol C

1. Prepare IsoCode®chemically treated cotton matrix paper samples as per steps 1-7 in the basic protocol (as described in Comparative protocol A).
2. Assemble lower portion (plates 250, 248, 246) of electroelution jig 240. DNA to pass to electrode 252 (the positive electrode).
3. Place IsoCode® chemically treated cotton matrix paper into sample well electroelution jig 240.
4. Add filtered distilled water to top of well.
5. Add 100 Da cellulose acetate membrane.
6. Assemble upper potion of jig 240 (plates 244, 242) to lower portion. Add filtered distilled water to well.
7. Insert upper electrode 152 into jig 240.
8. Apply voltage to electrodes 248 (negative electrode) and 252 (positive electrode) for 5 minutes.
9. Remove voltage source. (Alternatively, the upper electrode may be reverse-biased momentarily to drive off any nucleic acid components that may be adhered to electrode 252.
10. Remove electrodes 252. Remove eluate containing nucleic acids from well and place in 0.5-mL tube.
11. Discard paper and membrane(s).
12. The eluate is ready for PCR analysis.

The jig illustrated in FIGS. 18-23 was tested using electroelution conditions, as follows: voltage=(0.5, 1, 2, 5, 10, 20V), elution time=(1, 5, 10 minutes), buffer=water.

With respect to comparative protocol A, protocol C using electroelution could be completed in 5 minutes rather than in excess of 30 minutes, as a result of the elimination of the 30 minute heat step. Preliminary results indicated that the wash step (step 9) in comparative protocol A may not be required when employing protocol C.

Figure 24:
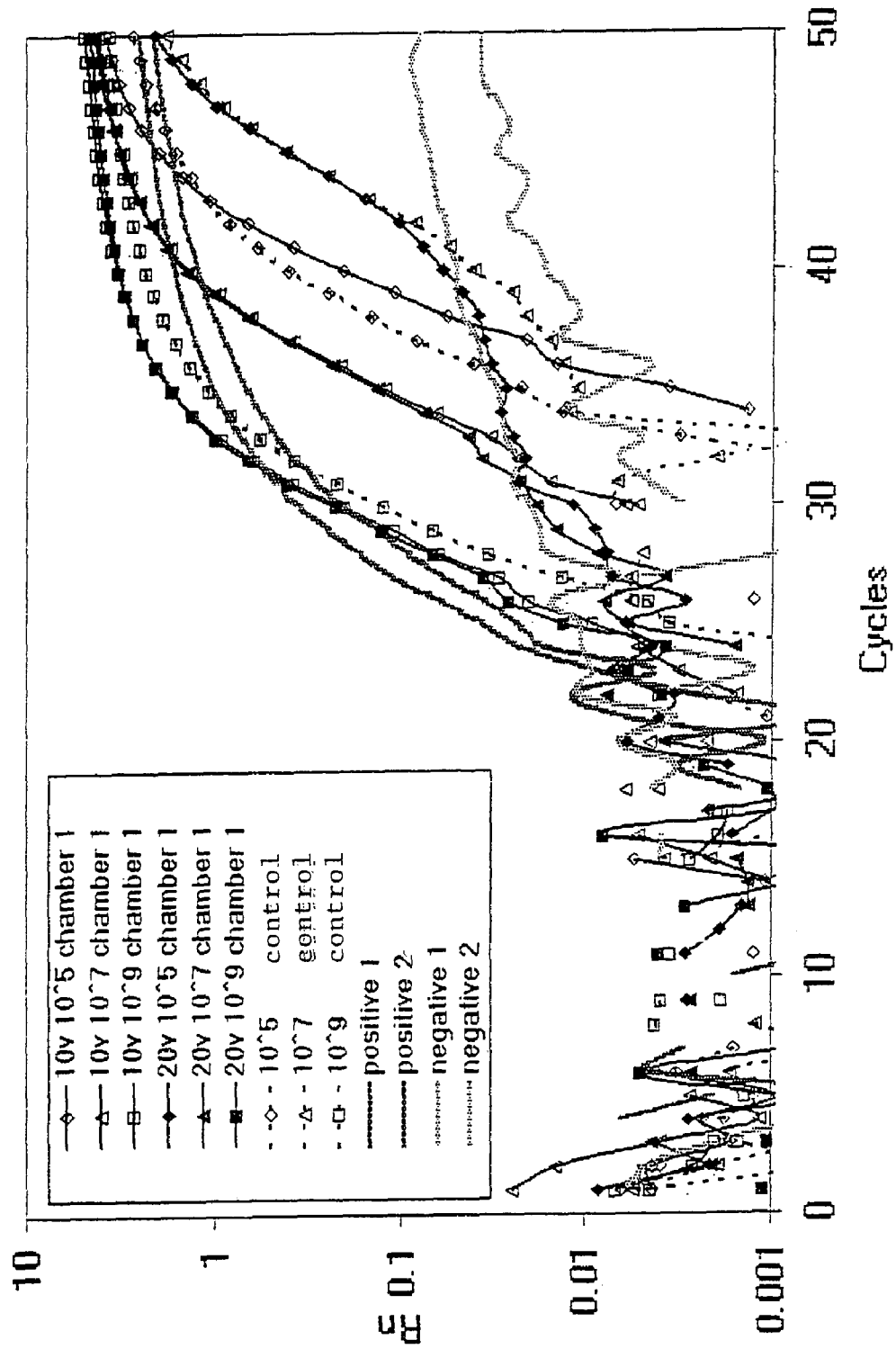
FIG. 24 is a series of plots showing detection improvements in analyzing samples prepared in a device such as described in FIGS. 19-23.

FIG. 24 shows results of an experiment conducted using an electroelution jig such as described above and shown in FIGS. 18-23, for the elution step, and an ABI PRISM 7700 Sequence Detection System for PCR amplication. Samples were vegetative bacterial cells seeded into a sandy soil. For the $10^9$ cell/gram level, there was an improvement of 7 cycles in detection cycle threshold. For the $10^5$ cell/gram seeded level, no improvement was seen in this experiment but that is sometimes typical due to statistical variation from sample to sample at the lower seeding levels. Results are shown in FIG. 24.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. An apparatus for preparing a nucleic acid component of a sample for amplification, comprising:
   a) a porous support including an agent that deactivates a nucleic acid amplification inhibitor component of a sample contacting the porous support;
   b) a housing having an opening and defining an interior, said interior being in fluid communication with the porous support, whereby at least a portion of a fluid directed through the opening is directed through at least a portion of the porous support thereby separating at least a portion of a nucleic acid component of a sample contacting the porous support from the sample, thereby preparing the nucleic acid component for amplification, the housing being attached to a first support; and
   c) a separating system for extracting the nucleic acid component from at least a portion of the sample and for depositing the nucleic acid component at the porous support wherein said separating system includes a magnetic substrate, and further includes:
      i. a vessel attached to a second support and having an inlet at a first end and an outlet at a second end, distal to said first end;
      ii. a rupturable ampoule contained within the vessel, wherein the magnetic substrate is contained within said ampoule when the ampoule is in an unruptured state;
      iii. a valve at the second end of the vessel including a well; and
      iv. a magnet at said valve;

wherein the first support and the second support are attached to the valve, and the well of the valve is in fluid communication with the outlet at the second end of the vessel when the valve is in a first position and in fluid communication with the porous support and the opening of the housing when the valve is in a second position, whereby the magnetic substrate is brought into contact with the porous support when the valve is in the second position.

2. The apparatus of claim 1, wherein said separating system includes a buffer in said ampoule, when the ampoule is in an unruptured state.

3. The apparatus of claim 1, wherein the magnetic substrate is selected from the group consisting of magnetic beads, shavings, and pellets.

4. The apparatus of claim 3, wherein the valve is rotatable, whereby the magnetic beads can be moved from the outlet at the second end of the vessel to the opening of the housing and thereby placed into contact with the porous support.

5. The apparatus of claim 4, wherein the magnet is removable from the valve, whereby the magnetic beads can be attracted to the magnet while the valve is in the first position, and whereby the magnet can be removed and the magnetic beads released into contact with the porous support while the valve is in the second position.

6. The apparatus of claim 5, further including a removable cap at the first end of the vessel.

7. The apparatus of claim 5, wherein the magnet is positioned to attract the magnetic beads in the vessel toward the outlet of the vessel.

8. The apparatus of claim 1, wherein the housing is detachable from the first support.

9. The apparatus of claim 1, wherein the magnetic substrate is coated with streptavidin.

\* \* \* \* \*